(12) United States Patent
Lorenz et al.

(10) Patent No.: US 6,852,497 B2
(45) Date of Patent: Feb. 8, 2005

(54) METHODS OF IDENTIFYING COMPOUNDS WHICH INHIBIT BINDING OF SLIC-1 TO PSGL-1

(75) Inventors: Meike Lorenz, Arlington, MA (US); Ron Kriz, Hudson, MA (US); Nadine Weich, Brookline, MA (US); Gray D. Shaw, Milton, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

(21) Appl. No.: 09/816,697

(22) Filed: Mar. 23, 2001

(65) Prior Publication Data

US 2002/0037840 A1 Mar. 28, 2002

Related U.S. Application Data

(60) Provisional application No. 60/192,104, filed on Mar. 24, 2000.

(51) Int. Cl.$^7$ .................. G01N 33/53; C07K 14/705
(52) U.S. Cl. .................. 435/7.1; 435/4; 530/350
(58) Field of Search .................. 435/4, 7.1; 530/350

(56) References Cited

U.S. PATENT DOCUMENTS 5,843,707 A  12/1998  Larsen et al. .............. 435/69.1

FOREIGN PATENT DOCUMENTS

| WO | WO 94/10309 | 5/1994 | ............ C12N/15/12 |
|---|---|---|---|
| WO | WO 00/58473 | 10/2000 | ............ C12N/15/12 |

OTHER PUBLICATIONS

Insug et al. Peptide 23: 999–1010, 2002.*
Blanck et al. J. Biol. Chem. 271: 7289–7292, 1996.*
Kogan et al. J Biol Chem. 270: 14047–14055, 1995.*
Structure and Mechanism in Protein Science Alan Fersht (ED) W.H. Freeman and Company N.Y. pp. 33–34.*
Kricka (ED) Ligand–Binder Assays Marcel Dekker, Inc. NY pp. 1–3.*
Skolnick et al. Trends in Biotechnologh 18: 34–39, 2000.*
Ngo et al. In The Protein Folding Problem and Tertiary Structure Prediction, 1994, Merz et al.(ED) Birkhauser, Boston MA pp. 433, 492–495.*
Kuntz Science 257: 1078–1082, 1992.*
Alonso–Lebrero, J.L., et al., "Polarization and interaction of adhesion molecules P–selectin glycoprotein ligand 1 and intercellular adhesion molecule 3 with moesin and ezrin in myeloid cells," Blood, vol. 95, No. 7:2413–2419, Apr. 1, 2000.
Sako, Dianne, et al., "Expression Cloning of a Functional Glycoprotein Ligand for P–Selectin," Cell, vol. 75: 1179–1186, Dec. 17, 1993.

Snapp, K.R., et al., "The cytoplasmic tail of P–selectin glycoprotein ligand–1 (PSGL–1) is required for optimal interactions with P–selectin" FASEB Journal, vol. 14, No. 6:A1146, Apr. 20, 2000 XP002186365.
XP002186366 Abstract Database EMBL [Online] HS1186915, accession No. AA282390, Apr. 4, 1997.
XP002186367 Abstract Database EMBL [Online] accession No. AW134842, Oct. 29, 1999.
XP002186368 Abstract Database EMBL [Online] accession No. AC007608, May 21, 1999.
Bevilacqua, M. P. et aaaaal., "Selectins," J. Clin. Invest. 91(2):379–87 (1993) retrieved from Internet on Mar. 21, 2000 at gateway.ovid.com.
Evangelista V. et al., "Platelet/polymorphonuclear leukocyte interaction: P–selectin triggers protein–tyrosine phosphorylation–dependent CD11b/CD18 adhesion: role of PSGL–1 as a signaling molecule," Blood, Feb. 1, 1999;93(3):876–85.
Gyuris, J. et al., "Cdi1, a human G1 and S phase protein phosphatase that associates with Cdk2," Cell Nov. 19, 1993;75(4):791–803.
Harris, E.S. et al., "A novel syndrome of variant leukocyte adhesion deficiency involving defects in adhesion mediated by beta1 and beta2 integrins," Blood Feb. 1, 2001;97(3):767–76.
Hildt, E. et al., "Identification of Grb2 as a novel binding partner of tumor necrosis factor (TNF) receptor I," J. Exp. Med., Jun. 7, 1999;189(11):1707–14.
Hidari, K. I.–P.J. et al., "Engagement of P–selectin glycoprotein ligand–1 enhances tyrosine phosphorylation and activates mitogen–activated protein kinases in human neutrophils," J. Biol. Chem., Nov. 7, 1997;272(45):28750–6.
Lowe, J.B. et al., "Therapeutic inhibition of carbohydrate–protein interactions in vivo," J. Clin. Invest., 99(5):822–26 (1997) retrieved from Internet on Mar. 21, 2000 at http://gateway.ovid.com.

(List continued on next page.)

*Primary Examiner*—Phillip Gambel
(74) *Attorney, Agent, or Firm*—Finnegan, Henderson, Farabow, Garrett & Dunner LLP

(57) ABSTRACT

The invention provides isolated nucleic acids molecules, designated SLIC-1 nucleic acid molecules, which encode novel P-selectin glycoprotein ligand (PSGL-1) binding molecules. The invention also provides antisense nucleic acid molecules, recombinant expression vectors containing SLIC-1 nucleic acid molecules, host cells into which the expression vectors have been introduced, and nonhuman transgenic animals in which a SLIC-1 gene has been introduced or disrupted. The invention still further provides isolated SLIC-1 proteins, fusion proteins, antigenic peptides and anti-SLIC-1 antibodies. Diagnostic methods utilizing compositions of the invention are also provided.

48 Claims, 5 Drawing Sheets

OTHER PUBLICATIONS

McEver, R.P. et al., "Role of PSGL–1 binding to selectins in leukocyte recruitment," *J. Clin. Invest.* 100(3):485–91 (1997) retrieved from Internet on Mar. 20, 2000 at gateway.ovid.com.

Sako, D. C. et al., "Expression cloning of a functional glycoprotein ligand for P–selectin," *Cell,* Dec. 17, 1993;75(6):1179–86.

Schievella, A. et al., "MADD, a novel death domain protein that interacts with the type 1 tumor necrosis factor receptor and activates mitogen–activated protein kinase," *J. Biol. Chem.,* May 2, 1997;272(18):12069–75.

Varki, A., "Selectin ligands: Will the real ones please stand up" *J. Clin. Invest.,* 99(2):158–62 (1997) retrieved from Internet on Mar. 21, 2000 at gateway.ovid.com.

\* cited by examiner

```
atg gca agt cca gag cac cct ggg agc cct ggc tgc atg gga ccc aca    48
Met Ala Ser Pro Glu His Pro Gly Ser Pro Gly Cys Met Gly Pro Ile
 1               5                  10                  15 acc cag tgc acg gca agg acc cag cag gaa gca cca gcc act ggc ccc    96
Thr Gln Cys Thr Ala Arg Thr Gln Gln Glu Ala Pro Ala Thr Gly Pro
             20                  25                  30 gac ctc ccg cac cca gga cct gac ggg cac tta gac aca cac agt ggc   144
Asp Leu Pro His Pro Gly Pro Asp Gly His Leu Asp Thr His Ser Gly
         35                  40                  45 ctg agc tcc aac tcc agc atg acc acg cgg gag ctt cag cag tac tgg   192
Leu Ser Ser Asn Ser Ser Met Thr Thr Arg Glu Leu Gln Gln Tyr Trp
     50                  55                  60 cag aac cag aaa tgc cgc tgg aag cac gtc aaa ctg ctc ttt gag atc   240
Gln Asn Gln Lys Cys Arg Trp Lys His Val Lys Leu Leu Phe Glu Ile
 65                  70                  75                  80 gct tca gct cgc atc gag gag aga aaa gtc tct aag ttt gtg gtg tac   288
Ala Ser Ala Arg Ile Glu Glu Arg Lys Val Ser Lys Phe Val Val Tyr
                 85                  90                  95 caa atc atc gtc atc cag act ggg agc ttt gac aac aac aag gcc gtc   336
Gln Ile Ile Val Ile Gln Thr Gly Ser Phe Asp Asn Asn Lys Ala Val
             100                 105                 110 ctg gaa cgg cgc tat tcc gac ttc gcg aag ctc cag aaa gcg ctg ctg   384
Leu Glu Arg Arg Tyr Ser Asp Phe Ala Lys Leu Gln Lys Ala Leu Leu
         115                 120                 125 aag acg ttc agg gag gag atc gaa gac gtg gag ttt ccc agg aag cac   432
Lys Thr Phe Arg Glu Glu Ile Glu Asp Val Glu Phe Pro Arg Lys His
     130                 135                 140 ctg act ggg aac ttc gct gag gag atg atc tgt gag cgt cgg cgc gcc   480
Leu Thr Gly Asn Phe Ala Glu Glu Met Ile Cys Glu Arg Arg Arg Ala
145                 150                 155                 160 ctg cag gag tac ctg ggc ctg ctc tac gcc atc cgc tgc gtg cgc cgc   528
Leu Gln Glu Tyr Leu Gly Leu Leu Tyr Ala Ile Arg Cys Val Arg Arg
                 165                 170                 175 tcc cgg gag ttc ctg gac ttc ctc acg cgg ccg gag ctg cgc gag gct   576
Ser Arg Glu Phe Leu Asp Phe Leu Thr Arg Pro Glu Leu Arg Glu Ala
             180                 185                 190 ttc ggc tgc ctg cgg gcc ggc cag tac ccg cgc gcc ctg gag ctg ctg   624
Phe Gly Cys Leu Arg Ala Gly Gln Tyr Pro Arg Ala Leu Glu Leu Leu
         195                 200                 205 ctg cgc gtg ctg ccg ctg cag gag aag ctc acc gcc cac tgc cct gcg   672
Leu Arg Val Leu Pro Leu Gln Glu Lys Leu Thr Ala His Cys Pro Ala
     210                 215                 220 gcc gcc gtc ccg gcc ctg tgc gcc gtg ctg ctg tgc cac cgc gac ctc   720
Ala Ala Val Pro Ala Leu Cys Ala Val Leu Leu Cys His Arg Asp Leu
225                 230                 235                 240
```

FIGURE 1A

```
gac cgc ccc gcc gag gcc ttc gcg gcc gga gag agg gcc ctg cag cgc    768
Asp Arg Pro Ala Glu Ala Phe Ala Ala Gly Glu Arg Ala Leu Gln Arg
            245             250                 255 ctg cag gcc cgg gag ggc cat cgc tac tat gcg cct ctg ctg gac gcc    816
Leu Gln Ala Arg Glu Gly His Arg Tyr Tyr Ala Pro Leu Leu Asp Ala
            260             265                 270 atg gtc cgc ctg gcc tac gcg ctg ggc aag gac ttc gtg act ctg cag    864
Met Val Arg Leu Ala Tyr Ala Leu Gly Lys Asp Phe Val Thr Leu Gln
            275             280                 285 gag agg ctg gag gag agc cag ctc cgg agg ccc acg ccc cga ggc atc    912
Glu Arg Leu Glu Glu Ser Gln Leu Arg Arg Pro Thr Pro Arg Gly Ile
            290             295                 300 acc ctg aag gag ctc act gtg cga gaa tac ctg cac tga                951
Thr Leu Lys Glu Leu Thr Val Arg Glu Tyr Leu His
305                 310                 315
```

FIGURE 1B

Genomic exon-intron boundary structure of the human SLIC-1 gene

```
Exon 1 - GAGACTGGAG -86                                             87- CCTTGGAGCA - EXON 2
         ||||||||||                                                     ||||||||||
         GAGACTGGAGgtcagtattt ...... Intron 1 (3651bp) ...... cctctggcagCCTTGGAGCA Exon 2 - CGGGCACTTA -224                                           225- ACACACACAG - EXON 3
         ||||||||||                                                     ||||||||||
         CGGGCACTTAgtgggctt ...... Intron 2 (1474bp) ...... gtccttccagACACACACAG Exon 3 - TAAGTTTGTG -377                                           378- GTGTACCAAA - EXON 4
         ||||||||||                                                     ||||||||||
         TAAGTTTGTGgtaagcagag ...... Intron 3 (1695bp) ...... tgcgccctagGTGTACCAAA
```

Genomic exon-intron boundary structure of the mouse SLIC-1 gene

```
Exon 1 - TCCCAGGTCA                                                     CCTTGGAGCA - EXON 2
         ||||||||||                                                     ||||||||||
         TCCCAGGTCAgtcagtgttt......       Intron 1      ...........gctcaggtagCCTTGGAGCA Exon 2 - GGATCAGAAA                                                     CTCAGGTAGC - EXON 3
         ||||||||||                                                     ||||||||||
         GGATCAGAAAggtaaactgg............ Intron 2      ...........ctcttgtagCTCAGGTAGC Exon 3 - CAAGTTTGTG                                                     ATGTACCAAG - EXON 4
         ||||||||||                                                     ||||||||||
         CAAGTTTGTGgtaagcagag............ Intron 3      ...........ctgcctgcagATGTACCAAG
```

FIGURE 4

SEQUENCE LISTING

```
<160> NUMBER OF SEQ ID NOS: 6

<210> SEQ ID NO 1
<211> LENGTH: 951
<212> TYPE: DNA
<213> ORGANISM: Homo sapiens

<400> SEQUENCE: 1
atggcaagtc cagagcaccc tgggagccct ggctgcatgg gacccataac ccagtgcacg      60
gcaaggaccc agcaggaagc accagccact ggccccgacc tcccgcaccc aggacctgac     120
gggcacttag acacacacag tggcctgagc tccaactcca gcatgaccac gcgggagctt     180
cagcagtact ggcagaacca gaaatgccgc tggaagcacg tcaaactgct ctttgagatc     240
gcttcagctc gcatcgagga gagaaaagtc tctaagtttg tggtgtacca aatcatcgtc     300
atccagactg ggagctttga caacaacaag gccgtcctgg aacggcgcta ttccgacttc     360
```

-continued

```
gcgaagctcc agaaagcgct gctgaagacg ttcagggagg agatcgaaga cgtggagttt      420
cccaggaagc acctgactgg gaacttcgct gaggagatga tctgtgagcg tcggcgcgcc      480
ctgcaggagt acctgggcct gctctacgcc atccgctgcg tgcgccgctc ccggagttc       540 ctggacttcc tcacgcggcc ggagctgcgc gaggctttcg gctgcctgcg ggccggccag      600
tacccgcgcg ccctggagct gctgctgcgc gtgctgccgc tgcaggagaa gctcaccgcc      660
cactgccctg cggccgccgt cccggccctg tgcgccgtgc tgctgtgcca ccgcgacctc      720
gaccgccccg ccgaggcctt cgcggccgga gagagggccc tgcagcgcct gcaggcccgg      780
gagggccatc gctactatgc gcctctgctg gacgccatgg tccgcctggc ctacgcgctg      840
ggcaaggact tcgtgactct gcaggagagg ctggaggaga ccagctccg gaggcccacg       900 ccccgaggca tcaccctgaa ggagctcact gtgcgagaat acctgcactg a               951
```

<210> SEQ ID NO 2
<211> LENGTH: 316
<212> TYPE: PRT
<213> ORGANISM: Homo sapiens

<400> SEQUENCE: 2

```
Met Ala Ser Pro Glu His Pro Gly Ser Pro Gly Cys Met Gly Pro Ile
 1               5                  10                  15

Thr Gln Cys Thr Ala Arg Thr Gln Glu Ala Pro Ala Thr Gly Pro
             20                  25                  30

Asp Leu Pro His Pro Gly Pro Asp Gly His Leu Asp Thr His Ser Gly
             35                  40                  45

Leu Ser Ser Asn Ser Ser Met Thr Thr Arg Glu Leu Gln Gln Tyr Trp
 50                  55                  60

Gln Asn Gln Lys Cys Arg Trp Lys His Val Lys Leu Phe Glu Ile
 65                  70                  75                  80

Ala Ser Ala Arg Ile Glu Glu Arg Lys Val Ser Lys Phe Val Tyr
                 85                  90                  95
Gln Ile Ile Val Ile Gln Thr Gly Ser Phe Asp Asn Asn Lys Ala Val
                100                 105                 110

Leu Glu Arg Arg Tyr Ser Asp Phe Ala Lys Leu Gln Lys Ala Leu Leu
            115                 120                 125

Lys Thr Phe Arg Glu Glu Ile Glu Asp Val Glu Phe Pro Arg Lys His
130                 135                 140

Leu Thr Gly Asn Phe Ala Glu Glu Met Ile Cys Glu Arg Arg Ala
145                 150                 155                 160

Leu Gln Glu Tyr Leu Gly Leu Leu Tyr Ala Ile Arg Cys Val Arg Arg
                165                 170                 175

Ser Arg Glu Phe Leu Asp Phe Leu Thr Arg Pro Glu Leu Arg Glu Ala
            180                 185                 190

Phe Gly Cys Leu Arg Ala Gly Gln Tyr Pro Arg Ala Leu Glu Leu Leu
        195                 200                 205

Leu Arg Val Leu Pro Leu Gln Glu Lys Leu Thr Ala His Cys Pro Ala
210                 215                 220

Ala Ala Val Pro Ala Leu Cys Ala Val Leu Leu Cys His Arg Asp Leu
225                 230                 235                 240

Asp Arg Pro Ala Glu Ala Phe Ala Ala Gly Glu Arg Ala Leu Gln Arg
                245                 250                 255

Leu Gln Ala Arg Glu Gly His Arg Tyr Tyr Ala Pro Leu Leu Asp Ala
            260                 265                 270

Met Val Arg Leu Ala Tyr Ala Leu Gly Lys Asp Phe Val Thr Leu Gln
```

-continued

```
                  275                 280                 285
Glu Arg Leu Glu Glu Ser Gln Leu Arg Arg Pro Thr Pro Arg Gly Ile
    290                 295                 300

Thr Leu Lys Glu Leu Thr Val Arg Glu Tyr Leu His
305                 310                 315

<210> SEQ ID NO 3
<211> LENGTH: 34
<212> TYPE: DNA
<213> ORGANISM: Artificial sequence
<220> FEATURE:
<223> OTHER INFORMATION: Primer

<400> SEQUENCE: 3
atactgaatt ccgcctctcc cgcaagggcc acat                              34

<210> SEQ ID NO 4
<211> LENGTH: 33
<212> TYPE: DNA
<213> ORGANISM: Artificial sequence
<220> FEATURE:
<223> OTHER INFORMATION: primer

<400> SEQUENCE: 4
atacaggatc cagagtgagc taagggagga aag                               33

<210> SEQ ID NO 5
<211> LENGTH: 15
<212> TYPE: PRT
<213> ORGANISM: Artificial sequence
<220> FEATURE:
<223> OTHER INFORMATION: antigen

<400> SEQUENCE: 5

Gln Glu Arg Leu Glu Glu Ser Gln Leu Arg Arg Pro Thr Pro Arg
1               5                   10                  15

<210> SEQ ID NO 6
<211> LENGTH: 11
<212> TYPE: PRT
<213> ORGANISM: Artificial sequence
<220> FEATURE:
<223> OTHER INFORMATION: T7 tag

<400> SEQUENCE: 6

Met Ala Ser Met Thr Gly Gly Gln Gln Met Gly
1               5                   10
```

METHODS OF IDENTIFYING COMPOUNDS WHICH INHIBIT BINDING OF SLIC-1 TO PSGL-1

RELATED APPLICATIONS

This application claims priority to U.S. Provisional Patent Application No. 60/192,104 filed on Mar. 24, 2000, incorporated herein in its entirety by reference.

BACKGROUND OF THE INVENTION

A multistep process involving adhesive and signaling events regulates inflammatory responses to infection or tissue injury. During inflammation leukocytes adhere to the vascular endothelium and enter subendothelial tissue, an interaction which is mediated by specific binding of the selectin or LEC-CAM class of proteins to ligands on target cells (Lowe, J B et al. 1997 *J. Clin. Invest.* 99:822–826). Such selectin-mediated cellular adhesion also occurs in thrombotic disorders and parasitic diseases and may be implicated in metastatic spread of tumor cells (Lowe, J B et al. 1997 *J. Clin. Invest.* 99:822–826).

The selectin proteins are characterized by a N-terminal lectin-like domain, an epidermal growth factor-like domain, and regions of homology to complement binding proteins (Bevilacqua, M P et al. 1993 *J. Clin. Invest.* 91:379–387). Thus far three human selectin proteins have been identified, E-selectin (formerly ELAM-1), L-selectin (formerly LAM-1) and P-selectin (formerly PADGEM or GMP-140). E-selectin is induced on endothelial cells several hours after activation by cytokines, mediating the calcium-dependent interaction between neutrophils and the endothelium. L-selectin is the lymphocyte homing receptor, and P-selectin rapidly appears on the cell surface of platelets when they are activated, mediating calcium-dependent adhesion of neutrophils or monocytes to platelets. P-selectin is also found in the Weibel-Palade bodies of endothelial cells; upon its release from these vesicles P-selectin mediates early binding of neutrophils to histamine- or thrombin-stimulated endothelium.

Selectins are believed to mediate adhesion through specific interactions with ligands present on the surface of target cells (Varki, A. J. 1997 *J. Clin. Invest.* 99:158–162). Generally the ligands of selectins are comprised at least in part of a carbohydrate moiety (e.g., sialyl Lewis$^x$ and sialyl Lewis$^a$, heparan sulfate) and each selectin appears to bind to a range of carbohydrates with varying affinities. The strength of the selectin mediated adhesive event (binding affinity) may also depend on the density of the carbohydrate and on the density of the selectin on the cell surface. For example, P-selectin binds to carbohydrates containing the non-sialated form of the Lewis$^x$ blood group antigen and with higher affinity to sialyl Lewis$^x$. P-selectin may also recognize sulfatides, which are heterogeneous 3-sulfated galactosyl ceramides, isolated from myeloid and tumor cells by lipid-extraction. In addition, the PSGL-1 glycoprotein acts as a ligand for P-selectin on human endothelial cells and platelets (U.S. Pat. No. 5,827,817).

The initial tethering of leukocytes to activated platelets or endothelium is in part mediated by PSGL-1/CD162. PSGL-1 is a mucin-like glycoprotein, expressed on the surface of most cells of hematopoietic origin, which functions as a cellular adhesion molecule. It normally exists as a disulfide linked homodimer with an apparent molecular weight of approximately 240 kD. PSGL-1 is a unique high affinity ligand for P-selectin and is one of several known lower affinity ligands for E-selectin and L-selectin. PSGL-1 has an extracellular domain rich in serines, theronines, and prolines, and which includes 15 decameric repeats, as well as putative sites for tyrosine sulfation (McEver, R P et al. 1997 *J. Clin. Invest.* 100:485–491). Binding of PSGL-1 to P-selectin requires that PSGL-1 be modified with alpha 2,3-linked sialic acid and alpha 1,3-linked fusose. In addition, PSGL-1 contains a single extracellular cysteine residue located at the junction of the transmembrane domain, followed by a cytoplasmic domain containing putative phosphorylation sites on tyrosine, threonine and serine residues. Comparison of the human and murine PSGL-1 proteins indicates that the transmembrane and cytoplasmic domains are highly conserved, implying an important function for these domains.

Various reports provide evidence that ligation of PSGL-1 on the surface of different cell types, by a variety of agents, results in an intracellular signaling event, including the phosphorylation of multiple intracellular proteins. Moreover, the binding of P-selectin to PSGL-1 may generate signals that are integrated with signals from other mediators to elicit an effector response. For example, the exposure of human monocytes in vitro to immobilized P-selectin has been reported to increase their response to the chemokine RANTES (Hidari, KI-P et al. 1997 *J. Biol. Chem.* 272:28750–28756). In polymorphonuclear leukocytes (PMNs), PSGL-1 mediated signaling events include activation of MAP kinases and the Ras GTPase, Interleukin-8 (IL-8) secretion, and the rapid tyrosine phosphorylation of a 110 kD protein also associated with the activation of the β2-integrin CD11b/CD18 (Evangelista, V et al. 1999 Blood 93:876–885; Hidari, KI-P et al. 1997 *J. Biol. Chem.* 272:28750–28756). In addition, adhesion of T lymphocytes to P-selectin has been reported to induce tyrosine phosphorylation of several intracellular proteins including the focal adhesion kinase, pp125FAK (McEver, R P et al. 1997 *J. Clin. Invest.* 100:485–491). A patient having a variant of leukocyte adhesion deficiency type 1 (LAD-1 variant) syndrome, which causes defects in leukocyte adhesion mediated by B1 and B2 integrins, has been reported. The neutrophils from this patient have a 77% increase in the surface expression of PSGL-1. The mechanism and genetic basis of this individuals' abnormality have not yet been characterized (Harris, E. S. et al. (2001) Blood 97:767–776).

Furthermore, upon leukocyte activation, PSGL-1 can redistribute to the uropods of polarized cells, and may thus interact with cytoskeletal elements during cellular redistribution (McEver, R P et al. 1997 *J. Clin. Invest.* 100:485–491). The adherence of hematopoietic progenitor cells (HPCs) bearing PSGL-1 on their surface has also been reported to inhibit cell growth and induce apoptosis under certain conditions.

To date, however, there has been no identification of the proximal molecule(s) that interact with the cytoplasmic domain of PSGL-1 and potentially mediate the intracellular signal transduction subsequent to the extracellular ligation of PSGL-1 and/or the cytoskeletal association of PSGL-1.

SUMMARY OF THE INVENTION

The present invention is based, at least in part, on the discovery of novel members of the SLIC-1 (for Selectin Ligand Interactor Cytoplasmic) family of molecules, referred to herein as SLIC-1 nucleic acid and protein molecules. The SLIC-1 molecules of the present invention are useful as targets for developing modulating agents to regulate a variety of cellular processes. Accordingly, in one aspect, this invention provides isolated nucleic acid molecules encoding SLIC-1 proteins or biologically active portions thereof, as well as nucleic acid fragments suitable as primers or hybridization probes for the detection of SLIC-1-encoding nucleic acids.

In one embodiment, a SLIC-1 nucleic acid molecule of the invention is at least 50%, 55%, 60%, 65%, 70%, 75%, 80%, 85%, 90%, 95%, 96%, 97%, 98%, or more identical to the nucleotide sequence (e.g., to the entire length of the nucleotide sequence) shown in SEQ ID NO:1, or a complement thereof. In a preferred embodiment, the isolated nucleic acid molecule includes the nucleotide sequence shown in SEQ ID NO:1, or a complement thereof. In another preferred embodiment, the nucleic acid molecule consists of the nucleotide sequence shown in SEQ ID NO:1. In another preferred embodiment, the nucleic acid molecule includes a fragment of at least 50, 100, 150, 200, 250, 300, 350, 400, 450, 500, 550, 600, 650, 700, 750, 800, 850, or 900 nucleotides (e.g., contiguous nucleotides) of the nucleotide sequence of SEQ ID NO: 1, or a complement thereof.

In another embodiment, a SLIC-1 nucleic acid molecule includes a nucleotide sequence encoding a protein having an amino acid sequence sufficiently identical to the amino acid sequence of SEQ ID NO:2. In a preferred embodiment, a SLIC-1 nucleic acid molecule includes a nucleotide sequence encoding a protein having an amino acid sequence at least 50%, 55%, 60%, 65%, 70%, 75%, 80%, 85%, 90%, 95%, 96%, 97%, 98%, 99% or more identical to the entire length of the amino acid sequence of SEQ ID NO:2.

In another preferred embodiment, an isolated nucleic acid molecule encodes the amino acid sequence of human SLIC-1. In yet another preferred embodiment, the nucleic acid molecule includes a nucleotide sequence encoding a protein having the amino acid sequence of SEQ ID NO:2. In yet another preferred embodiment, the nucleic acid molecule is at least 50, 100, 150, 200, 250, 300, 350, 400, 450, 500, 550, 600, 650, 700, 750, 800, 850, or 900 nucleotides in length. In a further preferred embodiment, the nucleic acid molecule is at least 50, 100, 150, 200, 250, 300, 350, 400, 450, 500, 550, 600, 650, 700, 750, 800, 850, or 900 nucleotides in length and encodes a protein having a SLIC-1 activity (as described herein).

Another embodiment of the invention features nucleic acid molecules, preferably SLIC-1 nucleic acid molecules, which specifically detect SLIC-1 nucleic acid molecules relative to nucleic acid molecules encoding non-SLIC-1 proteins. For example, in one embodiment, such a nucleic acid molecule is at least 50, 100, 150, 200, 250, 300, 350, 400, 450, 500, 550, 600, 650, 700, 750, 800, 850, 900 or more nucleotides in length and hybridizes under stringent conditions to a nucleic acid molecule comprising the nucleotide sequence shown in SEQ ID NO:1, or a complement thereof.

In other preferred embodiments, the nucleic acid molecule encodes a naturally occurring allelic variant of a polypeptide comprising the amino acid sequence of SEQ ID NO:2, wherein the nucleic acid molecule hybridizes to a nucleic acid molecule comprising SEQ ID NO:1 under stringent conditions.

Another embodiment of the invention provides an isolated nucleic acid molecule which is antisense to a SLIC-1 nucleic acid molecule, e.g., the coding strand of a SLIC-1 nucleic acid molecule.

Another aspect of the invention provides a vector comprising a SLIC-1 nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a SLIC-1 protein, by culturing in a suitable medium, a host cell, e.g., a mammalian host cell such as a non-human mammalian cell, of the invention containing a recombinant expression vector, such that the protein is produced.

Another aspect of this invention features isolated or recombinant SLIC-1 proteins and polypeptides. In one embodiment, an isolated SLIC-1 protein includes at least one immunoreceptor tyrosine-based activation motif (ITAM).

In a preferred embodiment, a SLIC-1 protein includes at least one immunoreceptor tyrosine-based activation motif and has an amino acid sequence at least about 50%, 55%, 60%, 65%, 70%, 75%, 80%, 85%, 90%, 95%, 96%, 97%, 98%, 99% or more identical to the amino acid sequence of SEQ ID NO:2.

In another preferred embodiment, a SLIC-1 protein includes at least one immunoreceptor tyrosine-based activation motif and has a SLIC-1 activity (as described herein).

In yet another preferred embodiment, a SLIC-1 protein includes at least one immunoreceptor tyrosine-based activation motif and is encoded by a nucleic acid molecule having a nucleotide sequence which hybridizes under stringent hybridization conditions to a nucleic acid molecule comprising the nucleotide sequence of SEQ ID NO:1.

In another embodiment, the invention features fragments of the protein having the amino acid sequence of SEQ ID NO:2, wherein the fragment comprises at least 15 amino acids (e.g., 15 contiguous amino acids) of the amino acid sequence of SEQ ID NO:2. In one embodiment, a SLIC-1 protein has amino acid residues 1–88 of SEQ ID NO:2. In another embodiment, a SLIC-1 protein has amino acid residues 1–60 of SEQ ID NO:2. In a further embodiment, a SLIC-1 protein has amino acid residues 1–226 of SEQ ID NO:2. In another embodiment, a SLIC-1 protein has the amino acid sequence of SEQ ID NO:2.

In another embodiment, the invention features a SLIC-1 protein which is encoded by a nucleic acid molecule consisting of a nucleotide sequence at least about 50%, 55%, 60%, 65%, 70%, 75%, 80%, 85%, 90%, 95%, 96%, 97%, 98%, 99% or more identical to a nucleotide sequence of SEQ ID NO:1, or a complement thereof. This invention further features a SLIC-1 protein, which is encoded by a nucleic acid molecule consisting of a nucleotide sequence which hybridizes under stringent hybridization conditions to a nucleic acid molecule comprising the nucleotide sequence of SEQ ID NO:1, or a complement thereof.

The proteins of the present invention or portions thereof, e.g., biologically active portions thereof, can be operatively linked to a non-SLIC-1 polypeptide (e.g., heterologous amino acid sequences) to form fusion proteins. The invention further features antibodies, such as monoclonal or polyclonal antibodies, that specifically bind proteins of the invention, preferably SLIC-1 proteins. In addition, the SLIC-1 proteins or biologically active portions thereof can be incorporated into pharmaceutical compositions, which optionally include pharmaceutically acceptable carriers.

In another aspect, the present invention provides a method for detecting the presence of a SLIC-1 nucleic acid molecule, protein, or polypeptide in a biological sample by contacting the biological sample with an agent capable of detecting a SLIC-1 nucleic acid molecule, protein, or polypeptide such that the presence of a SLIC-1 nucleic acid molecule, protein or polypeptide is detected in the biological sample.

In another aspect, the present invention provides a method for detecting the presence of SLIC-1 activity in a biological sample by contacting the biological sample with an agent capable of detecting an indicator of SLIC-1 activity such that the presence of SLIC-1 activity is detected in the biological sample.

In another aspect, the invention provides a method for modulating SLIC-1 activity comprising contacting a cell capable of expressing SLIC-1 with an agent that modulates SLIC-1 activity such that SLIC-1 activity in the cell is modulated. In one embodiment, the agent inhibits SLIC-1 activity. In another embodiment, the agent stimulates SLIC-1 activity. In one embodiment, the agent is an antibody that specifically binds to a SLIC-1 protein. In another embodiment, the agent modulates expression of SLIC-1 by modulating transcription of a SLIC-1 gene or translation of a SLIC-1 mRNA. In yet another embodiment, the agent is a nucleic acid molecule having a nucleotide sequence that is antisense to the coding strand of a SLIC-1 mRNA or a SLIC-1 gene.

In one embodiment, the methods of the present invention are used to treat a subject having a disorder characterized by aberrant or unwanted SLIC-1 protein or nucleic acid expression or activity by administering an agent which is a SLIC-1 modulator to the subject. In one embodiment, the SLIC-1 modulator is a SLIC-1 protein. In another embodiment the SLIC-1 modulator is a SLIC-1 nucleic acid molecule. In yet another embodiment, the SLIC-1 modulator is a peptide, peptidomimetic, or other small molecule. In a preferred embodiment, the disorder characterized by aberrant or unwanted SLIC-1 protein or nucleic acid expression is a inflammatory or immune system disorder. In another preferred embodiment, the disorder characterized by aberrant or unwanted SLIC-1 protein or nucleic acid expression is a cardiovascular disorder. In another embodiment, the disorder characterized by aberrant or unwanted SLIC-1 activity is a cellular proliferation, activation, adhesion, growth, differentiation, or migration disorder. In a further embodiment, the disorder characterized by aberrant or unwanted SLIC-1 activity is a hematopoietic or thrombotic disorder.

The present invention also provides diagnostic assays for identifying the presence or absence of a genetic alteration characterized by at least one of (i) aberrant modification or mutation of a gene encoding a SLIC-1 protein; (ii) mis-regulation of the gene; and (iii) aberrant post-translational modification of a SLIC-1 protein, wherein a wild-type form of the gene encodes a protein with a SLIC-1 activity.

In another aspect the invention provides methods for identifying a compound that binds to or modulates the activity of a SLIC-1 protein, by providing an indicator composition comprising a SLIC-1 protein having SLIC-1 activity, contacting the indicator composition with a test compound, and determining the effect of the test compound on SLIC-1 activity in the indicator composition to identify a compound that modulates the activity of a SLIC-1 protein.

Other features and advantages of the invention will be apparent from the following detailed description and claims.

BRIEF DESCRIPTION OF THE DRAWINGS

FIGS. 1A and 1B depict the cDNA sequence and predicted amino acid sequence of human SLIC-1. The nucleotide sequence corresponds to nucleic acids 1 to 951 of SEQ ID NO:1. The amino acid sequence corresponds to amino acids 1 to 316 of SEQ ID NO: 2.

FIG. 4 depicts the genomic structures of the human and mouse SLIC-1 genes, which were determined by blast analysis of genomic sequences with human SLIC-1 cDNA sequence. The SLIC-1 gene is composed of four exons in both species and the exon-intron boundaries have been conserved. The human intron sizes and exon positions in cDNA (shown) were determined using full length human cDNA and complete gene sequence.

DETAILED DESCRIPTION OF THE INVENTION

Figure 2:
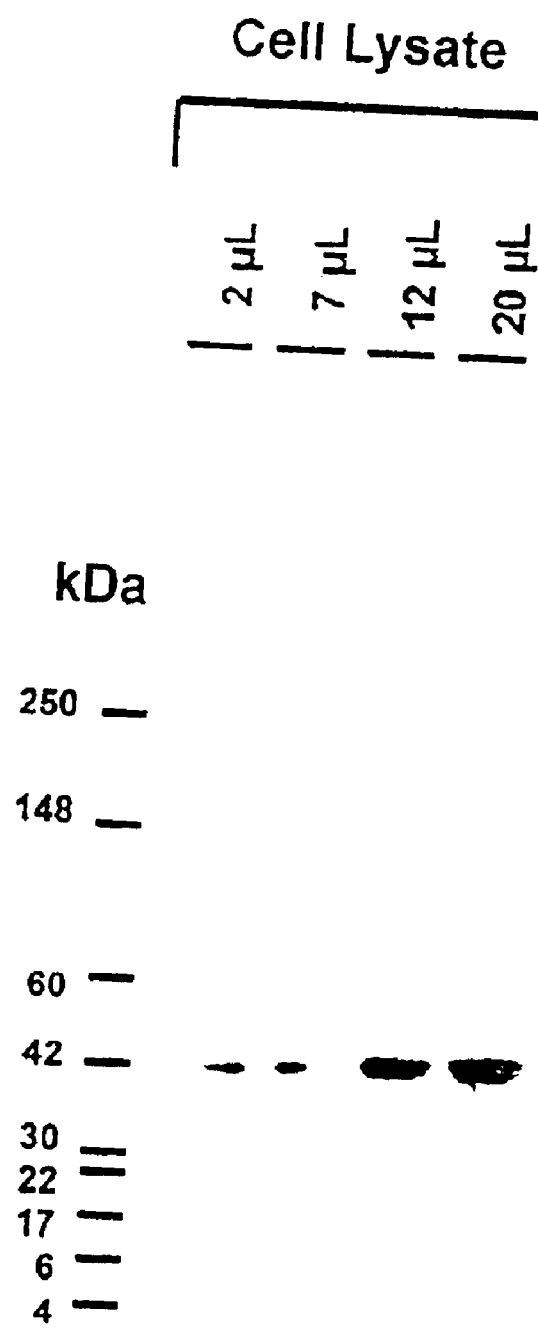
FIG. 2 depicts the transient over-expression of SLIC-1 in COS cells as assessed by Western blot analysis.

The present invention is based, at least in part, on the discovery of novel molecules, referred to herein as SLIC-1 nucleic acid and protein molecules, which are novel members of the SLIC (for Selectin Ligand Interactor Cytoplasmic) family of molecules.

As used herein, the term, "selectin ligand interactor cytoplasmic-1" or "SLIC-1" molecule includes a protein or polypeptide which binds to or interacts with the cytoplasmic domain of a selectin glycoprotein ligand (e.g., PSGL-1) or a selectin protein. SLIC-1 molecules are typically expressed in cells of hematopoietic origin, and participate in intracellular signal transduction pathways, e.g., signals transduced by PSGL-1. In addition, SLIC-1 molecules can interact with effector molecules (e.g., molecules containing an SH2 domain), as well as mediate the interaction of proteins (e.g., PSGL-1) with the cytoskeleton.

These novel molecules are capable of, for example, modulating a selectin glycoprotein ligand, e.g., a P-selectin glycoprotein ligand (PSGL-1), mediated activity in a cell, e.g., a hematopoietic or myeloid cell, and thus may play a role in a variety of cellular processes, e.g., signal transduction, cytoskeletal organization, immune and inflammatory responses, inter- and intra-cellular communication, adhesion, migration, cell activation, growth, differentiation, and proliferation. Thus, the SLIC-1 proteins of the present invention provide novel diagnostic targets and therapeutic agents to control or modulate selectin ligand interactor cytoplasmic-1 molecule-associated disorders, e.g., an inflammatory or immune system disorder, a cardiovascular disorder, a cellular proliferation, activation, adhesion, growth, differentiation, or migration disorder, or a hematopoietic or thrombotic disorder. Moreover, as the SLIC-1 proteins of the present invention can bind to or interact with and modulate selectin glycoprotein ligand, e.g., P-selectin glycoprotein ligand (PSGL-1), mediated activities, they may be useful for developing novel diagnostic and therapeutic agents for disorders associated with or related to aberrant PSGL-1 activity, e.g., an inflammatory or immune system disorder, or a disorder associated with aberrant cell migration and/or adhesion.

As used herein, a "selectin glycoprotein ligand mediated activity" a "PSGL-1 mediated activity", or a "PSGL-1 activity" includes an activity which involves a P-selectin glycoprotein ligand, e.g., a P-selectin glycoprotein ligand on an endothelial cell, a hematopoietic cell, or a leukocyte. P-selectin glycoprotein ligands participate in intercellular adhesion (e.g., leukocyte adhesion to the vasculature), intracellular signal transduction, cytoskeletal organization, immune and inflammatory responses, cell activation, and cell migration.

As used herein, a "selectin ligand interactor cytoplasmic-1 molecule-associated disorder" or a "SLIC-1 associated disorder" includes a disorder, disease or condition which is characterized by a misregulation (e.g., upregulation or downregulation) of a selectin ligand interactor cytoplasmic-1 (SLIC-1) molecule activity. Selectin ligand interactor cytoplasmic-1 (SLIC-1) molecule-associated disorders can detrimentally affect cell functions such as signal transduction, cytoskeletal organization, inter- and intracellular communication, adhesion, migration, cell activation, growth, differentiation, and proliferation. Examples of selectin ligand interactor cytoplasmic-1 (SLIC-1) molecule-associated disorders include inflammatory or immune system disorders, examples of which include, but are not limited to inflammatory bowel disease, ulcerative colitis, Crohn's disease, leukocyte adhesion deficiency II syndrome, peritonitis, lung inflammation, asthma, acute appendicitis, septic shock, nephritis, amyloidosis, rheumatoid arthritis, sarcoidosis, scleroderma, lupus, polymyositis, Reiter's syndrome, psoriasis, pelvic inflammatory disease, inflammatory breast disease, orbital inflammatory disease, immune deficiency disorders (e.g., HIV, common variable immunodeficiency, severe combined immunodeficiency), autoimmune disorders, and neurodegenerative diseases (e.g., Alzheimer's disease).

A selectin ligand interactor cytoplasmic-1 (SLIC-1) molecule-associated disorder also includes a hematopoietic or thrombotic disorder, for example, disseminated intravascular coagulation, anemia, lymphoma, leukemia, neutrophilia, neutropenia, myeloproliferative disorders, thrombocytosis, thrombocytopenia, vonWillebrand disease, and hemophilia.

Further examples of selectin ligand interactor cytoplasmic-1 (SLIC-1) molecule-associated disorders include cardiac-related disorders. Cardiovascular system disorders in which the SLIC-1 molecules of the invention may be directly or indirectly involved include arteriosclerosis, ischemia reperfusion injury, inflammatory heart disease, restenosis, arterial inflammation, vascular wall remodeling, coronary microembolism, congestive heart failure, cardiomyopathy, coronary artery ligation, vascular heart disease, angina, hypertension, myocardial infarction, coronary artery disease, and atherosclerosis.

Further examples of selectin ligand interactor cytoplasmic-1 (SLIC-1) molecule-associated disorders include cellular proliferation, activation, adhesion, growth, differentiation, or migration disorders. A "cellular proliferation, activation, adhesion, growth, differentiation, or migration disorder" includes those disorders that affect cell proliferation, activation, adhesion, growth, differentiation, or migration processes. As used herein, a "cellular proliferation, activation, adhesion, growth, differentiation, or migration process" is a process by which a cell increases in number, size, activation state, or content, by which a cell develops a specialized set of characteristics which differ from that of other cells, or by which a cell moves closer to or further from a particular location or stimulus. The SLIC-1 molecules of the present invention may be involved in signal transduction mechanisms which are known to be involved in cellular activation, adhesion, migration, growth, proliferation, differentiation, and apoptosis processes. Thus, the SLIC-1 molecules may modulate cellular growth, activation, adhesion, differentiation, or migration, and may play a role in disorders characterized by aberrantly regulated growth, activation, adhesion, differentiation, or migration. Such disorders include cancer, e.g., carcinoma, sarcoma, or leukemia; tumor angiogenesis and metastasis; and hematopoietic and/or myeloproliferative disorders.

SLIC-1-associated or related disorders also include disorders of tissues in which SLIC-1 protein is expressed, e.g., hematopoietic cells. Such disorders include, for example, inflammatory and/or immune system disorders, hematopoietic, or thrombotic disorders.

As used herein, a "selectin ligand interactor cytoplasmic-1 molecule activity" or a "SLIC-1 activity" includes an activity which involves binding or interacting with the cytoplasmic domain of a selectin glycoprotein ligand (e.g., PSGL-1) or a selectin protein and transducing a signal, e.g., via an effector molecule. In addition, a SLIC-1 activity includes an activity which involves mediating the interaction of a protein (e.g., PSGL-1) with the cytoskeleton. The SLIC-1 molecules of the present invention may be important in cellular processes such as signal transduction, cytoskeletal organization, immune and inflammatory responses, inter- and intra-cellular communication, adhesion, migration, cell activation, growth, differentiation, and proliferation.

The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin, e.g., monkey proteins. Members of a family may also have common functional characteristics.

For example, the family of SLIC-1 proteins comprises at least one "immunoreceptor tyrosine-based activation motif" (ITAM) in the protein molecule or the nucleic acid molecule encoding the protein molecule. As used herein, the term "immunoreceptor tyrosine-based activation motif" includes a protein motif having an amino acid sequence of about 10–25 amino acid residues. More preferably, a immunoreceptor tyrosine-based activation motif includes at least about 15–20 amino acid residues. The immunoreceptor tyrosine-based activation motif is characterized by conserved tyrosine residues. In one embodiment, an immunoreceptor tyrosine-based activation motif comprises at least one, and more preferably two, tyrosine residues. In another embodiment, an immunoreceptor tyrosine-based activation motif comprises at least two or more tyrosine residues. In one embodiment, an immunoreceptor tyrosine-based activation motif serves as a SH2 domain binding site, thereby forming the structural basis for interactions with downstream effector molecules which mediate signal transduction. Immunoreceptor tyrosine-based activation motifs are described in, for example, Isakov, N (1998) *Receptors Channels* 5:243–253; Isakov, N (1997) *J. Leuk. Biol.* 61:6–16; and Chan, A C et al. (1996) *Curr. Opin. Immunol.* 8:394–401, the contents of which are incorporated herein by reference. Accordingly, SLIC-1 proteins having at least 50–60% homology, preferably about 60–70%, more preferably about 70–80%, or about 80–90% homology with a immunoreceptor tyrosine-based activation motif of human SLIC-1 are within the scope of the invention.

Isolated proteins of the present invention, preferably SLIC-1 proteins, have an amino acid sequence sufficiently identical to the amino acid sequence of SEQ ID NO:2 or are encoded by a nucleotide sequence sufficiently identical to SEQ ID NO:1. As used herein, the term "sufficiently identical" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%–80%, and even more preferably 90–95% homology across the amino acid sequences of the domains and contain at least one and preferably two structural domains or motifs, are defined herein as sufficiently identical. Furthermore, amino acid or nucleotide sequences which share at least 30%, 40%, or 50%, preferably 60%, more preferably 70–80%, or 90–95% homology and share a common functional activity are defined herein as sufficiently identical.

As used interchangeably herein, an "SLIC-1 activity", "biological activity of SLIC-1" or "functional activity of SLIC-1", refers to an activity exerted by a SLIC-1 protein, polypeptide or nucleic acid molecule on a SLIC-1 responsive cell or tissue, or on a SLIC-1 protein substrate, as determined in vivo, or in vitro, according to standard techniques. In one embodiment, a SLIC-1 activity is a direct activity, such as an association with a SLIC-1-target molecule. As used herein, a "target molecule" or "binding partner" is a molecule with which a SLIC-1 protein binds or interacts in nature, such that SLIC-1-mediated function is achieved. A SLIC-1 target molecule can be a non-SLIC-1 molecule or a SLIC-1 protein or polypeptide of the present invention. In an exemplary embodiment, a SLIC-1 target molecule is a SLIC-1 substrate, e.g., a intracellular signaling molecule, preferably containing an SH2 domain. In another embodiment, a SLIC-1 substrate is a cytoskeletal protein or a cytoskeletal-associated protein. Alternatively, a SLIC-1 activity is an indirect activity, such as a cellular signaling activity mediated by interaction of the SLIC-1 protein with a SLIC-1 substrate. The biological activities of SLIC-1 are described herein. For example, the SLIC-1 proteins of the present invention can have one or more of the following activities: (1) interacting with a non-SLIC-1 protein molecule; (2) activating a SLIC-1-dependent signal transduction pathway; (3) modulating a PSGL-1-dependent signal transduction pathway; (4) modulating intercellular adhesion; (5) modulating PSGL-1 association with the cytoskeleton; (6) modulating cell activation and/or proliferation; and (7) modulating cell migration.

Accordingly, another embodiment of the invention features isolated SLIC-1 proteins and polypeptides having a SLIC-1 activity. Preferred proteins are SLIC-1 proteins having at least one immunoreceptor tyrosine-based activation motif, and, preferably, a SLIC-1 activity.

Additional preferred proteins have at least one immunoreceptor tyrosine-based activation motif, and are, preferably, encoded by a nucleic acid molecule having a nucleotide sequence which hybridizes under stringent hybridization conditions to a nucleic acid molecule comprising the nucleotide sequence of SEQ ID NO:1.

The nucleotide sequence of the isolated human SLIC-1 cDNA and the predicted amino acid sequence of the human SLIC-1 polypeptide are shown in FIGS. 1A and 1B and in SEQ ID NOs:1 and 2, respectively.

The human SLIC-1 gene, which is approximately 951 nucleotides in length, encodes a protein having a molecular weight of approximately 34.8 kD and which is approximately 316 amino acid residues in length.

Various aspects of the invention are described in further detail in the following subsections:

I. Isolated Nucleic Acid Molecules

One aspect of the invention pertains to isolated nucleic acid molecules that encode SLIC-1 proteins or biologically active portions thereof as well as nucleic acid fragments sufficient for use as hybridization probes to identify SLIC-1-encoding nucleic acid molecules (e.g., SLIC-1 mRNA) and fragments for use as PCR primers for the amplification or mutation of SLIC-1 nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated SLIC-1 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule; can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, or a portion thereof, can be isolated using standard molecular biology techniques and the sequence information provided herein. Using all or portion of the nucleic acid sequence of SEQ ID NO:1, as a hybridization probe, SLIC-1 nucleic acid molecules can be isolated using standard hybridization and cloning techniques (e.g., as described in Sambrook, J., Fritch, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989). Moreover, a nucleic acid molecule encompassing all or a portion of SEQ ID NO:1 can be isolated by the polymerase chain reaction (PCR) using synthetic oligonucleotide primers designed based upon the sequence of SEQ ID NO:1.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to SLIC-1 nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human SLIC-1 cDNA. This cDNA comprises sequences encoding the human SLIC-1 protein (i.e., "the coding region", from nucleotides 1–951).

In another preferred embodiment, an isolated nucleic acid molecule of the invention comprises a nucleic acid molecule which is a complement of the nucleotide sequence shown in SEQ ID NO:1, or a portion of any of these nucleotide sequences. A nucleic acid molecule which is complementary to the nucleotide sequence shown in SEQ ID NO:1, is one which is sufficiently complementary to the nucleotide sequence shown in SEQ ID NO:1, such that it can hybridize to the nucleotide sequence shown in SEQ ID NO:1 thereby forming a stable duplex.

In still another preferred embodiment, an isolated nucleic acid molecule of the present invention comprises a nucleotide sequence which is at least about 50%, 55%, 60%, 65%, 70%, 75%, 80%, 85%, 90%, 95%, 96%, 97%, 98%, 99% or more identical to the entire length of the nucleotide sequence shown in SEQ ID NO:1, or a portion of any of these nucleotide sequences.

Moreover, the nucleic acid molecule of the invention can comprise only a portion of the nucleic acid sequence of SEQ ID NO:1, for example, a fragment which can be used as a probe or primer or a fragment encoding a portion of a SLIC-1 protein, e.g., a biologically active portion of a SLIC-1 protein. The nucleotide sequence determined from the cloning of the SLIC-1 gene allows for the generation of probes and primers designed for use in identifying and/or cloning other SLIC-1 family members, as well as SLIC-1 homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, 75, 80, 85, 90, 95, 100, 150, or 200 or more consecutive nucleotides of a sense sequence of SEQ ID NO: 1, of an anti-sense sequence of SEQ ID NO:1, or of a naturally occurring allelic variant or mutant of SEQ ID NO: 1. In one embodiment, a nucleic acid molecule of the present invention comprises a nucleotide sequence which is greater than 50, 100, 150, 200, 250, 300, 350, 400, 450, 500, 550, 600, 650, 700, 750, 800, 850, 900 or more nucleotides in length and hybridizes under stringent hybridization conditions to a nucleic acid molecule of SEQ ID NO:1.

Probes based on the SLIC-1 nucleotide sequences can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a SLIC-1 protein, such as by measuring a level of a SLIC-1-encoding nucleic acid in a sample of cells from a subject e.g., detecting SLIC-1 mRNA levels or determining whether a genomic SLIC-1 gene has been mutated or deleted.

A nucleic acid fragment encoding a "biologically active portion of a SLIC-1 protein" can be prepared by isolating a portion of the nucleotide sequence of SEQ ID NO:1, which encodes a polypeptide having a SLIC-1 biological activity (the biological activities of the SLIC-1 proteins are described herein), expressing the encoded portion of the SLIC-1 protein (e.g., by recombinant expression in vitro) and assessing the activity of the encoded portion of the SLIC-1 protein.

The invention further encompasses nucleic acid molecules that differ from the nucleotide sequence shown in SEQ ID NO:1, due to degeneracy of the genetic code and thus encode the same SLIC-1 proteins as those encoded by the nucleotide sequence shown in SEQ ID NO:1. In another embodiment, an isolated nucleic acid molecule of the invention has a nucleotide sequence encoding a protein having an amino acid sequence shown in SEQ ID NO:2.

In addition to the SLIC-1 nucleotide sequences shown in SEQ ID NO:1, it will be appreciated by those skilled in the art that DNA sequence polymorphisms that lead to changes in the amino acid sequences of the SLIC-1 proteins may exist within a population (e.g., the human population). Such genetic polymorphism in the SLIC-1 genes may exist among individuals within a population due to natural allelic variation. As used herein, the terms "gene" and "recombinant gene" refer to nucleic acid molecules which include an open reading frame encoding a SLIC-1 protein, preferably a mammalian SLIC-1 protein, and can further include non-coding regulatory sequences, and introns.

Allelic variants of human SLIC-1 include both functional and non-functional SLIC-1 proteins. Functional allelic variants are naturally occurring amino acid sequence variants of the human SLIC-1 protein that maintain the ability to bind a SLIC-1 ligand or substrate and/or modulate, for example, inflammatory signaling mechanisms, PSGL-1 signal transduction, or cell adhesion. Functional allelic variants will typically contain only conservative substitution of one or more amino acids of SEQ ID NO:2, or substitution, deletion or insertion of non-critical residues in non-critical regions of the protein.

Non-functional allelic variants are naturally occurring amino acid sequence variants of the human SLIC-1 protein that do not have the ability to either bind a SLIC-1 ligand and/or modulate any of the SLIC-1 activities described herein. Non-functional allelic variants will typically contain a non-conservative substitution, a deletion, or insertion or premature truncation of the amino acid sequence of SEQ ID NO:2, or a substitution, insertion or deletion in critical residues or critical regions.

The present invention further provides non-human orthologues of the human SLIC-1 protein. Orthologues of the human SLIC-1 protein are proteins that are isolated from non-human organisms and possess the same SLIC-1 ligand binding and/or modulation of signal transduction, cytoskeletal association, or cell adhesion activities of the human SLIC-1 protein. Orthologues of-the human SLIC-1 protein can readily be identified as comprising an amino acid sequence that is substantially identical to SEQ ID NO:2.

Moreover, nucleic acid molecules encoding other SLIC-1 family members and, thus, which have a nucleotide sequence which differs from the SLIC-1 sequences of SEQ ID NO: 1. For example, another SLIC-1 cDNA can be identified based on the nucleotide sequence of human SLIC-1. Moreover, nucleic acid molecules encoding SLIC-1 proteins from different species, and which, thus, have a nucleotide sequence which differs from the SLIC-1 sequences of SEQ ID NO: 1. For example, a mouse SLIC-1 cDNA can be identified based on the nucleotide sequence of a human SLIC-1.

Nucleic acid molecules corresponding to natural allelic variants and homologues of the SLIC-1 cDNAs of the invention can be isolated based on their homology to the SLIC-1 nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the SLIC-1 cDNAs of the invention can further be isolated by mapping to the same chromosome or locus as the SLIC-1 gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1. In other embodiment, the nucleic acid is at least 50, 100, 150, 200, 250, 300, 350, 400, 450, 500, 550, 600, 650, 700, 750, 800, 850, 900 or more nucleotides in length.

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in *Current Protocols in Molecular Biology*, Ausubel et al., eds., John Wiley & Sons, Inc. (1995), sections 2, 4 and 6. Additional stringent conditions can be found in *Molecular Cloning: A Laboratory Manual*, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chloride/sodium citrate (SSC), at about 65–70° C. (or hybridization in 4×SSC plus 50% formamide at about 42–50° C.) followed by one or more washes in 1×SSC, at about 65–70° C. A preferred, non-limiting example of highly stringent hybridization conditions includes hybridization in 1×SSC, at about 65–70° C. (or hybridization in 1×SSC plus 50% formamide at about 42–50° C.) followed by one or more washes in 0.3×SSC, at about 65–70° C. A preferred, non-limiting example of reduced stringency hybridization conditions includes hybridization in 4×SSC, at about 50–60° C. (or alternatively hybridization in 6SSC plus 50% formamide at about 40–45° C.) followed by one or more washes in 2×SSC, at about 50–60° C. Ranges intermediate to the above-recited values, e.g., at 65–70° C. or at 42–50° C. are also intended to be encompassed by the present invention. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m(° C.)=2(\# \text{ of A+T bases})+4(\# \text{ of G+C bases})$. For hybrids between 18 and 49 base pairs in length, $T_m(° C.)=81.5+16.6(\log_{10}[Na^+])+0.41(\%G+C)-(600/N)$, where N is the number of bases in the hybrid, and $[Na^+]$ is the concentration of sodium ions in the hybridization buffer ($[Na^+]$ for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional preferred, non-limiting example of stringent hybridization conditions is hybridization in 0.25–0.5M $NaH_2PO_4$, 7% SDS at about 65° C., followed by one or more washes at 0.02M $NaH_2PO_4$, 1% SDS at 65° C., see e.g., Church and Gilbert (1984) *Proc. Natl. Acad. Sci. USA* 81: 1991–1995, (or alternatively 0.2×SSC, 1% SDS).

Preferably, an isolated nucleic acid molecule of the invention that hybridizes under stringent conditions to the sequence of SEQ ID NO:1 and corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the SLIC-1 sequences that may exist in the population, the skilled artisan will further appreciate that changes can be introduced by mutation into the nucleotide sequences of SEQ ID NO:1, thereby leading to changes in the amino acid sequence of the encoded SLIC-1 proteins, without altering the functional ability of the SLIC-1 proteins. For example, nucleotide substitutions leading to amino acid substitutions at "non-essential" amino acid residues can be made in the sequence of SEQ ID NO:1. A "non-essential" amino acid residue is a residue that can be altered from the wild-type sequence of SLIC-1 (e.g., the sequence of SEQ ID NO:2) without altering the biological activity, whereas an "essential" amino acid residue is required for biological activity. For example, amino acid residues that are conserved among the SLIC-1 proteins of the present invention, e.g., those present in a immunoreceptor tyrosine-based activation motif, are predicted to be particularly unamenable to alteration. Furthermore, additional amino acid residues that are conserved between the SLIC-1 proteins of the present invention and other members of the SLIC family are not likely to be amenable to alteration.

Accordingly, another aspect of the invention pertains to nucleic acid molecules encoding SLIC-1 proteins that contain changes in amino acid residues that are not essential for activity. Such SLIC-1 proteins differ in amino acid sequence from SEQ ID NO:2, yet retain biological activity. In one embodiment, the isolated nucleic acid molecule comprises a nucleotide sequence encoding a protein, wherein the protein comprises an amino acid sequence at least about 50%, 55%, 60%, 65%, 70%, 75%, 80%, 85%, 90%, 95%, 96%, 97%, 98%, 99% or more identical to SEQ ID NO:2.

An isolated nucleic acid molecule encoding a SLIC-1 protein identical to the protein of SEQ ID NO:2, can be created by introducing one or more nucleotide substitutions, additions or deletions into the nucleotide sequence of SEQ ID NO:1, such that one or more amino acid substitutions, additions or deletions are introduced into the encoded protein. Mutations can be introduced into SEQ ID NO:1 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a SLIC-1 protein is preferably replaced with another amino acid residue from the same side chain family. Alternatively, in another embodiment, mutations can be introduced randomly along all or part of a SLIC-1 coding sequence, such as by saturation mutagenesis, and the resultant mutants can be screened for SLIC-1 biological activity to identify mutants that retain activity. Following mutagenesis of SEQ ID NO:1, the encoded protein can be expressed recombinantly and the activity of the protein can be determined.

In a preferred embodiment, a mutant SLIC-1 protein can be assayed for the ability to (1) interact with a non-SLIC-1 protein molecule; (2) activate a SLIC-1-dependent signal transduction pathway; (3) modulate a PSGL-1-dependent signal transduction pathway; (4) modulate intercellular adhesion; (5) modulate PSGL-1 association with the cytoskeleton; (6) modulate cell activation and/or proliferation; and (7) modulate cell migration.

In addition to the nucleic acid molecules encoding SLIC-1 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire SLIC-1 coding strand, or to only a portion thereof. In one embodiment, an antisense nucleic acid molecule is antisense to a "coding region" of the coding strand of a nucleotide sequence encoding SLIC-1. The term "coding region" refers to the region of the nucleotide sequence comprising codons which are translated into amino acid residues (e.g., the coding region of human SLIC-1 corresponds to SEQ ID NO:1). In another embodiment, the antisense nucleic acid molecule is antisense to a "noncoding region" of the coding strand of a nucleotide sequence encoding SLIC-1. The term "noncoding region" refers to 5' and 3' sequences which flank the coding region that are not translated into amino acids (i.e., also referred to as 5' and 3' untranslated regions).

Given the coding strand sequences encoding SLIC-1 disclosed herein (e.g., SEQ ID NO:1), antisense nucleic acids of the invention can be designed according to the rules of Watson and Crick base pairing. The antisense nucleic acid molecule can be complementary to the entire coding region of SLIC-1 mRNA, but more preferably is an oligonucleotide which is antisense to only a portion of the coding or noncoding region of SLIC-1 mRNA. For example, the antisense oligonucleotide can be complementary to the region surrounding the translation start site of SLIC-1 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a SLIC-1 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585–591)) can be used to catalytically cleave SLIC-1 mRNA transcripts to thereby inhibit translation of SLIC-1 mRNA. A ribozyme having specificity for a SLIC-1-encoding nucleic acid can be designed based upon the nucleotide sequence of a SLIC-1 cDNA disclosed herein (i.e., SEQ ID NO:1). For example, a derivative of a Tetrahymena L-19 IVS RNA can be constructed in which the nucleotide sequence of the active site is complementary to the nucleotide sequence to be cleaved in a SLIC-1-encoding mRNA. See, e.g., Cech et al. U.S. Pat. No. 4,987,071; and Cech et al. U.S. Pat. No. 5,116,742. Alternatively, SLIC-1 mRNA can be used to select a catalytic RNA having a specific ribonuclease activity from a pool of RNA molecules. See, e.g., Bartel, D. and Szostak, J. W. (1993) Science 261:1411–1418.

Alternatively, SLIC-1 gene expression can be inhibited by targeting nucleotide sequences complementary to the regulatory region of the SLIC-1 (e.g., the SLIC-1 promoter and/or enhancers) to form triple helical structures that prevent transcription of the SLIC-1 gene in target cells. See generally, Helene, C. (1991) Anticancer Drug Des. 6(6):569–84; Helene, C. et al. (1992) Ann. N.Y. Acad. Sci. 660:27–36; and Maher, L. J. (1992) Bioassays 14(12):807–15.

In yet another embodiment, the SLIC-1 nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) Bioorganic & Medicinal Chemistry 4 (1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. Proc. Natl. Acad. Sci. 93: 14670–675.

PNAs of SLIC-1 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of SLIC-1 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of SLIC-1 can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of SLIC-1 nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) Nucleic Acids Res. 24 (17): 3357–63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used between the PNA and the 5' end of DNA (Mag, M. et al. (1989) Nucleic Acid Res. 17: 5973–88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) Bioorganic Med. Chem. Lett. 5: 1119–11124).

In other embodiments, the oligonucleotide may include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) Bio-Techniques 6:958–976) or intercalating agents. (See, e.g., Zon (1988) Pharm. Res. 5:539–549). To this end, the oligonucleotide may be conjugated to another molecule, (e.g., a peptide, hybridization triggered cross-linking agent, transport agent, or hybridization-triggered cleavage agent).

Alternatively, the expression characteristics of an endogenous SLIC-1 gene within a cell line or microorganism may be modified by inserting a heterologous DNA regulatory element into the genome of a stable cell line or cloned microorganism such that the inserted regulatory element is operatively linked with the endogenous SLIC-1 gene. For example, an endogenous SLIC-1 gene which is normally "transcriptionally silent", i.e., a SLIC-1 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous SLIC-1 gene may be activated by insertion of a promiscuous regulatory element that works across cell types.

A heterologous regulatory element may be inserted into a stable cell line or cloned microorganism, such that it is operatively linked with an endogenous SLIC-1 gene, using techniques, such as targeted homologous recombination, which are well known to those of skill in the art, and described, e.g., in Chappel, U.S. Pat. No. 5,272,071; PCT publication No. WO 91/06667, published May 16, 1991.

II. Isolated SLIC-1 Proteins and Anti-SLIC-1 Antibodies

One aspect of the invention pertains to isolated SLIC-1 proteins, and biologically active portions thereof, as well as polypeptide fragments suitable for use as immunogens to raise anti-SLIC-1 antibodies. In one embodiment, native SLIC-1 proteins can be isolated from cells or tissue sources by an appropriate purification scheme using standard protein purification techniques. In another embodiment, SLIC-1 proteins are produced by recombinant DNA techniques. Alternative to recombinant expression, a SLIC-1 protein or polypeptide can be synthesized chemically using standard peptide synthesis techniques.

An "isolated" or "purified" protein or biologically active portion thereof is substantially free of cellular material or other contaminating proteins from the cell or tissue source from which the SLIC-1 protein is derived, or substantially free from chemical precursors or other chemicals when chemically synthesized. The language "substantially free of cellular material" includes preparations of SLIC-1 protein in which the protein is separated from cellular components of the cells from which it is isolated or recombinantly produced. In one embodiment, the language "substantially free of cellular material" includes preparations of SLIC-1 protein having less than about 30% (by dry weight) of non-SLIC-1 protein (also referred to herein as a "contaminating protein"), more preferably less than about 20% of non-SLIC-1 protein, still more preferably less than about 10% of non-SLIC-1 protein, and most preferably less than about 5% non-SLIC-1 protein. When the SLIC-1 protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of SLIC-1 protein in which the protein is separated from chemical precursors or other chemicals which are involved in the synthesis of the protein. In one embodiment, the language "substantially free of chemical precursors or other chemicals" includes preparations of SLIC-1 protein having less than about 30% (by dry weight) of chemical precursors or non-SLIC-1 chemicals, more preferably less than about 20% chemical precursors or non-SLIC-1 chemicals, still more preferably less than about 10% chemical precursors or non-SLIC-1 chemicals, and most preferably less than about 5% chemical precursors or non-SLIC-1 chemicals.

As used herein, a "biologically active portion" of a SLIC-1 protein includes a fragment of a SLIC-1 protein which participates in an interaction between a SLIC-1 molecule and a non-SLIC-1 molecule. Biologically active portions of a SLIC-1 protein include peptides comprising amino acid sequences sufficiently identical to or derived from the amino acid sequence of the SLIC-1 protein, e.g., the amino acid sequence shown in SEQ ID NO:2, which include less amino acids than the full length SLIC-1 proteins, and exhibit at least one activity of a SLIC-1 protein. Typically, biologically active portions comprise a domain or motif with at least one activity of the SLIC-1 protein, e.g., modulating signal transduction, PSGL-1 association with the cytoskeleton, or cell adhesion. A biologically active portion of a SLIC-1 protein can be a polypeptide which is, for example, 25, 30, 35, 40, 45, 50, 75, 88, 100, 125, 150, 160, 175, 200, 226 or more amino acids in length. Biologically active portions of a SLIC-1 protein can be used as targets for developing agents which modulate a SLIC-1 mediated activity, e.g., modulation of signal transduction, PSGL-1 association with the cytoskeleton, or cell adhesion.

In one embodiment, a biologically active portion of a SLIC-1 protein comprises at least one immunoreceptor tyrosine-based activation motif. Moreover, other biologically active portions, in which other regions of the protein are deleted, can be prepared by recombinant techniques and evaluated for one or more of the functional activities of a native SLIC-1 protein.

In a preferred embodiment, the SLIC-1 protein has an amino acid sequence shown in SEQ ID NO:2. In other embodiments, the SLIC-1 protein is substantially identical to SEQ ID NO:2, and retains the functional activity of the protein of SEQ ID NO:2, yet differs in amino acid sequence due to natural allelic variation or mutagenesis, as described in detail in subsection I above. Accordingly, in another embodiment, the SLIC-1 protein is a protein which comprises an amino acid sequence at least about 50%, 55%, 60%, 65%, 70%, 75%, 80%, 85%, 90%, 95%, 96%, 97%, 98%, 99% or more identical to SEQ ID NO:2.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the SLIC-1 amino acid sequence of SEQ ID NO:2 having 316 amino acid residues, at least 95, preferably at least 126, more preferably at least 158, even more preferably at least 190, and even more preferably at least 221 or more amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller ((1988) *Comput. Appl. Biosci.* 4:11–17) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to SLIC-1 nucleic acid molecules of the invention. BLAST protein searches can be performed with the XBLAST program, score=100, wordlength=3 to obtain amino acid sequences homologous to SLIC-1 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

The invention also provides SLIC-1 chimeric or fusion proteins. As used herein, a SLIC-1 "chimeric protein" or "fusion protein" comprises a SLIC-1 polypeptide operatively linked to a non-SLIC-1 polypeptide. An "SLIC-1 polypeptide" refers to a polypeptide having an amino acid sequence corresponding to SLIC-1, whereas a "non-SLIC-1 polypeptide" refers to a polypeptide having an amino acid sequence corresponding to a protein which is not substantially homologous to the SLIC-1 protein, e.g., a protein which is different from the SLIC-1 protein and which is derived from the same or a different organism. Within a SLIC-1 fusion protein the SLIC-1 polypeptide can correspond to all or a portion of a SLIC-1 protein. In a preferred embodiment, a SLIC-1 fusion protein comprises at least one biologically active portion of a SLIC-1 protein. In another preferred embodiment, a SLIC-1 fusion protein comprises at least two biologically active portions of a SLIC-1 protein. Within the fusion protein, the term "operatively linked" is intended to indicate that the SLIC-1 polypeptide and the non-SLIC-1 polypeptide are fused in-frame to each other. The non-SLIC-1 polypeptide can be fused to the N-terminus or C-terminus of the SLIC-1 polypeptide.

For example, in one embodiment, the fusion protein is a GST-SLIC-1 fusion protein in which the SLIC-1 sequences are fused to the C-terminus of the GST sequences. In another embodiment, the fusion protein is a T7-SLIC-1 fusion protein in which the SLIC-1 sequences are fused to T7 sequences, e.g., a T7 protein tag (see Example 4). Such fusion proteins can facilitate the purification and/or detection of recombinant SLIC-1.

In another embodiment, the fusion protein is a SLIC-1 protein containing a heterologous signal sequence at its N-terminus. In certain host cells (e.g., mammalian host cells), expression and/or secretion of SLIC-1 can be increased through use of a heterologous signal sequence.

The SLIC-1 fusion proteins of the invention can be incorporated into pharmaceutical compositions and administered to a subject in vivo. The SLIC-1 fusion proteins can be used to affect the bioavailability of a SLIC-1 substrate. Use of SLIC-1 fusion proteins may be useful therapeutically for the treatment of disorders caused by, for example, (i) aberrant modification or mutation of a gene encoding a SLIC-1 protein; (ii) mis-regulation of the SLIC-1 gene; and (iii) aberrant post-translational modification of a SLIC-1 protein.

Moreover, the SLIC-1-fusion proteins of the invention can be used as immunogens to produce anti-SLIC-1 antibodies in a subject, to purify SLIC-1 ligands and in screening assays to identify molecules which inhibit the interaction of SLIC-1 with a SLIC-1 substrate.

Preferably, a SLIC-1 chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A SLIC-1-encoding nucleic acid can be cloned into such an expression vector such that the fusion moiety is linked in-frame to the SLIC-1 protein.

The present invention also pertains to variants of the SLIC-1 proteins which function as either SLIC-1 agonists (mimetics) or as SLIC-1 antagonists. Variants of the SLIC-1 proteins can be generated by mutagenesis, e.g., discrete point mutation or truncation of a SLIC-1 protein. An agonist of the SLIC-1 proteins can retain substantially the same, or a subset, of the biological activities of the naturally occurring form of a SLIC-1 protein. An antagonist of a SLIC-1 protein can inhibit one or more of the activities of the naturally occurring form of the SLIC-1 protein by, for example, competitively modulating a SLIC-1-mediated activity of a SLIC-1 protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the SLIC-1 protein.

In one embodiment, variants of a SLIC-1 protein which function as either SLIC-1 agonists (mimetics) or as SLIC-1 antagonists can be identified by screening combinatorial libraries of mutants, e.g., truncation mutants, of a SLIC-1 protein for SLIC-1 protein agonist or antagonist activity. In one embodiment, a variegated library of SLIC-1 variants is generated by combinatorial mutagenesis at the nucleic acid level and is encoded by a variegated gene library. A variegated library of SLIC-1 variants can be produced by, for example, enzymatically ligating a mixture of synthetic oligonucleotides into gene sequences such that a degenerate set of potential SLIC-1 sequences is expressible as individual polypeptides, or alternatively, as a set of larger fusion proteins (e.g., for phage display) containing the set of SLIC-1 sequences therein. There are a variety of methods which can be used to produce libraries of potential SLIC-1 variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential SLIC-1 sequences. Methods for synthesizing degenerate oligonucleotides are known in the art (see, e.g, Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a SLIC-1 protein coding sequence can be used to generate a variegated population of SLIC-1 fragments for screening and subsequent selection of variants of a SLIC-1 protein. In one embodiment, a library of coding sequence fragments can be generated by treating a double stranded PCR fragment of a SLIC-1 coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the SLIC-1 protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of SLIC-1 proteins. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify SLIC-1 variants (Arkin and Yourvan (1992) *Proc. Natl. Acad. Sci. USA* 89:7811–7815; Delgrave et al. (1993) *Protein Engineering* 6(3): 327–331).

In one embodiment, cell based assays can be exploited to analyze a variegated SLIC-1 library. For example, a library of expression vectors can be transfected into a cell line, e.g., a hematopoietic cell line, which ordinarily responds to a SLIC-1 ligand in a particular SLIC-1 ligand-dependent manner. The transfected cells are then contacted with a SLIC-1 ligand and the effect of expression of the mutant on, e.g., signal transduction, PSGL-1 association with the cytoskeleton, or cell adhesion can be detected. Plasmid DNA can then be recovered from the cells which score for inhibition, or alternatively, potentiation of signaling by the SLIC-1 ligand, and the individual clones further characterized.

An isolated SLIC-1 protein, or a portion or fragment thereof, can be used as an immunogen to generate antibodies that bind SLIC-1 using standard techniques for polyclonal and monoclonal antibody preparation. A full-length SLIC-1 protein can be used or, alternatively, the invention provides antigenic peptide fragments of SLIC-1 for use as immunogens. The antigenic peptide of SLIC-1 comprises at least 8 amino acid residues of the amino acid sequence shown in SEQ ID NO:2 and encompasses an epitope of SLIC-1 such that an antibody raised against the peptide forms a specific immune complex with SLIC-1. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of SLIC-1 that are located on the surface of the protein, e.g., hydrophilic regions, as well as regions with high antigenicity.

A SLIC-1 immunogen typically is used to prepare antibodies by immunizing a suitable subject, (e.g., rabbit, goat, mouse or other mammal) with the immunogen. An appropriate immunogenic preparation can contain, for example, recombinantly expressed SLIC-1 protein or a chemically synthesized SLIC-1 polypeptide. The preparation can further include an adjuvant, such as Freund's complete or incomplete adjuvant, or similar immunostimulatory agent. Immunization of a suitable subject with an immunogenic SLIC-1 preparation induces a polyclonal anti-SLIC-1 antibody response.

Accordingly, another aspect of the invention pertains to anti-SLIC-1 antibodies. The term "antibody" as used herein refers to immunoglobulin molecules and immunologically active portions of immunoglobulin molecules, i.e., molecules that contain an antigen binding site which specifically binds (immunoreacts with) an antigen, such as SLIC-1. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind SLIC-1. The term "monoclonal antibody" or "monoclonal antibody composition", as used herein, refers to a population of antibody molecules that contain only one species of an antigen binding site capable of immunoreacting with a particular epitope of SLIC-1. A monoclonal antibody composition thus typically displays a single binding affinity for a particular SLIC-1 protein with which it immunoreacts.

Polyclonal anti-SLIC-1 antibodies can be prepared as described above by immunizing a suitable subject with a SLIC-1 immunogen. For example, polyclonal anti-SLIC-1 antibodies were generated by immunizing rabbits with a SLIC-1 polypeptide antigen conjugated to KLH (see Example 3). The anti-SLIC-1 antibody titer in the immunized subject can be monitored over time by standard techniques, such as with an enzyme linked immunosorbent assay (ELISA) using immobilized SLIC-1. If desired, the antibody molecules directed against SLIC-1 can be isolated from the mammal (e.g., from the blood) and further purified by well known techniques, such as protein A chromatography to obtain the IgG fraction. At an appropriate time after immunization, e.g., when the anti-SLIC-1 antibody titers are highest, antibody-producing cells can be obtained from the subject and used to prepare monoclonal antibodies by standard techniques, such as the hybridoma technique originally described by Kohler and Milstein (1975) *Nature* 256:495–497) (see also, Brown et al. (1981) *J. Immunol.* 127:539–46; Brown et al. (1980) *J. Biol. Chem.* 255:4980–83; Yeh et al. (1976) *Proc. Natl. Acad. Sci. USA* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.* 3:231–36). Briefly, an immortal cell line (typically a myeloma) is fused to lymphocytes (typically splenocytes) from a mammal immunized with a SLIC-1 immunogen as described above, and the culture supernatants of the resulting hybridoma cells are screened to identify a hybridoma producing a monoclonal antibody that binds SLIC-1.

Any of the many well known protocols used for fusing lymphocytes and immortalized cell lines can be applied for the purpose of generating an anti-SLIC-1 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind SLIC-1, e.g., using a standard ELISA assay.

Alternative to preparing monoclonal antibody-secreting hybridomas, a monoclonal anti-SLIC-1 antibody can be identified and isolated by screening a recombinant combinatorial immunoglobulin library (e.g., an antibody phage display library) with SLIC-1 to thereby isolate immunoglobulin library members that bind SLIC-1. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J* 12:725–734; Hawkins et al. (1992) *J. Mol. Biol.* 226:889–896; Clarkson et al. (1991) *Nature* 352:624–628; Gram et al. (1992) *Proc. Natl. Acad. Sci. USA* 89:3576–3580; Garrad et al. (1991) *Bio/Technology* 9:1373–1377; Hoogenboom et al. (1991) *Nuc. Acid Res.* 19:4133–4137; Barbas et al. (1991) *Proc. Natl. Acad. Sci. USA* 88:7978–7982; and McCafferty et al. *Nature* (1990) 348:552–554.

Additionally, recombinant anti-SLIC-1 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173, 494; Neuberger et al. PCT International Publication No. WO 86/01533; Cabilly et al. U.S. Pat. No. 4,816,567; Cabilly et al. European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-SLIC-1 antibody (e.g., monoclonal antibody) can be used to isolate SLIC-1 by standard techniques, such as affinity chromatography or immunoprecipitation. An anti-SLIC-1 antibody can facilitate the purification of natural SLIC-1 from cells and of recombinantly produced SLIC-1 expressed in host cells. Moreover, an anti-SLIC-1 antibody can be used to detect SLIC-1 protein (e.g., in a cellular lysate or cell supernatant) in order to evaluate the abundance and pattern of expression of the SLIC-1 protein. Anti-SLIC-1 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding a SLIC-1 protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., SLIC-1 proteins, mutant forms of SLIC-1 proteins, fusion proteins, and the like).

The recombinant expression vectors of the invention can be designed for expression of SLIC-1 proteins in prokaryotic or eukaryotic cells. For example, SLIC-1 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in SLIC-1 activity assays, (e.g., direct assays or competitive assays described in detail below), or to generate antibodies specific for SLIC-1 proteins, for example. In a preferred embodiment, a SLIC-1 fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al, (1992) *Nucleic Acids Res.* 20:2111–2118). Such alteration of nucleic acid sequences of the invention can be carried out by standard DNA synthesis techniques.

In another embodiment, the SLIC-1 expression vector is a yeast expression vector. Examples of vectors for expression in yeast *S. cerevisiae* include pYepSec1 (Baldari, et al., (1987) *EMBO J*. 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp, San Diego, Calif.).

Alternatively, SLIC-1 proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol*. 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J*. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to SLIC-1 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a SLIC-1 nucleic acid molecule of the invention is introduced, e.g., a SLIC-1 nucleic acid molecule within a recombinant expression vector or a SLIC-1 nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a SLIC-1 protein can be expressed in bacterial cells such as *E. coli*, insect cells, yeast or mammalian cells (such as Chinese hamster ovary cells (CHO) or COS cells (see Examples 3 and 4)). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a SLIC-1 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a SLIC-1 protein. Accordingly, the invention further provides methods for producing a SLIC-1 protein using the host cells of the invention. In one embodiment, the method comprises culturing the host cell of the invention (into which a recombinant expression vector encoding a SLIC-1 protein has been introduced) in a suitable medium such that a SLIC-1 protein is produced. In another embodiment, the method further comprises isolating a SLIC-1 protein from the medium or the host cell.

The host cells of the invention can also be used to produce non-human transgenic animals. For example, in one embodiment, a host cell of the invention is a fertilized oocyte or an embryonic stem cell into which SLIC-1-coding sequences have been introduced. Such host cells can then be used to create non-human transgenic animals in which exogenous SLIC-1 sequences have been introduced into their genome or homologous recombinant animals in which endogenous SLIC-1 sequences have been altered. Such animals are useful for studying the function and/or activity of a SLIC-1 and for identifying and/or evaluating modulators of SLIC-1 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous SLIC-1 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a SLIC-1-encoding nucleic acid into the male pronuclei of a fertilized oocyte, e.g., by microinjection, retroviral infection, and allowing the oocyte to develop in a pseudopregnant female foster animal. The SLIC-1 cDNA sequence of SEQ ID NO:1 can be introduced as a transgene into the genome of a non-human animal. Alternatively, a nonhuman homologue of a human SLIC-1 gene, such as a mouse or rat SLIC-1 gene, can be used as a transgene. Alternatively, a SLIC-1 gene homologue, such as another SLIC-1 family member, can be isolated based on hybridization to the SLIC-1 cDNA sequences of SEQ ID NO:1 and used as a transgene. Intronic sequences and polyadenylation signals can also be included in the transgene to increase the efficiency of expression of the transgene. A tissue-specific regulatory sequence(s) can be operably linked to a SLIC-1 transgene to direct expression of a SLIC-1 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner at al. and in Hogan, B., Manipulating the Mouse Embryo, (Cold Spring Harbor Laboratory Press, Cold Spring Harbor, N.Y., 1986). Similar methods are used for production of other transgenic animals. A transgenic founder animal can be identified based upon the presence of a SLIC-1 transgene in its genome and/or expression of SLIC-1 mRNA in tissues or cells of the animals. A transgenic founder animal can then be used to breed additional animals carrying the transgene. Moreover, transgenic animals carrying a transgene encoding a SLIC-1 protein can further be bred to other transgenic animals carrying other transgenes.

To create a homologous recombinant animal, a vector is prepared which contains at least a portion of a SLIC-1 gene into which a deletion, addition or substitution has been introduced to thereby alter, e.g., functionally disrupt, the SLIC-1 gene. The SLIC-1 gene can be a human gene (e.g., the cDNA of SEQ ID NO:1), but more preferably, is a non-human homologue of a human SLIC-1 gene (e.g., a cDNA isolated by stringent hybridization with the nucleotide sequence of SEQ ID NO:1). For example, a mouse SLIC-1 gene can be used to construct a homologous recombination nucleic acid molecule, e.g., a vector, suitable for altering an endogenous SLIC-1 gene in the mouse genome. In a preferred embodiment, the homologous recombination nucleic acid molecule is designed such that, upon homologous recombination, the endogenous SLIC-1 gene is functionally disrupted (i.e., no longer encodes a functional protein; also referred to as a "knock out" vector). Alternatively, the homologous recombination nucleic acid molecule can be designed such that, upon homologous recombination, the endogenous SLIC-1 gene is mutated or otherwise altered but still encodes functional protein (e.g, the upstream regulatory region can be altered to thereby alter the expression of the endogenous SLIC-1 protein). In the homologous recombination nucleic acid molecule, the altered portion of the SLIC-1 gene is flanked at its 5' and 3' ends by additional nucleic acid sequence of the SLIC-1 gene to allow for homologous recombination to occur between the exogenous SLIC-1 gene carried by the homologous recombination nucleic acid molecule and an endogenous SLIC-1 gene in a cell, e.g., an embryonic stem cell. The additional flanking SLIC-1 nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) Cell 51:503 for a description of homologous recombination vectors). The homologous recombination nucleic acid molecule is introduced into a cell, e.g., an embryonic stem cell line (e.g., by electroporation) and cells in which the introduced SLIC-1 gene has homologously recombined with the endogenous SLIC-1 gene are selected (see e.g., Li, E. et al. (1992) Cell 69:915). The selected cells can then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) Current Opinion in Biotechnology 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) Proc. Natl. Acad. Sci. USA 89:6232–6236. Another example of a recombinase system is the FLP recombinase system of Saccharomyces cerevisiae (O'Gorman et al. (1991) Science 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) Nature 385:810–813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The SLIC-1 nucleic acid molecules, fragments of SLIC-1 proteins, and anti-SLIC-1 antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration.

The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a SLIC-1 protein or an anti-SLIC-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g, a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i. e,. including heteroorganic and organometallic compounds) having a molecular weight less than about 10,000 grams per mole, organic or inorganic compounds having a molecular weight less-than-about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a SLIC-1 protein of the invention has one or more of the following activities: (1) interacting with a non-SLIC-1 protein molecule; (2) activating a SLIC-1-dependent signal transduction pathway; (3) modulating a PSGL-1-dependent signal transduction pathway; (4) modulating intercellular adhesion; (5) modulating PSGL-1 association with the cytoskeleton; (6) modulating cell activation and/or proliferation; and (7) modulating cell migration.

The isolated nucleic acid molecules of the invention can be used, for example, to express SLIC-1 protein (e.g., via a recombinant expression vector in a host cell in gene therapy applications), to detect SLIC-1 mRNA (e.g., in a biological sample) or a genetic alteration in a SLIC-1 gene, and to modulate SLIC-1 activity, as described further below. The SLIC-1 proteins can be used to treat disorders characterized by insufficient or excessive production of a SLIC-1 substrate or production of SLIC-1 inhibitors. In addition, the SLIC-1 proteins can be used to screen for naturally occurring SLIC-1 substrates, to screen for drugs or compounds which modulate SLIC-1 activity, as well as to treat disorders characterized by insufficient or excessive production of SLIC-1 protein or production of SLIC-1 protein forms which have decreased, aberrant or unwanted activity compared to SLIC-1 wild type protein (e.g., P-selectin glycoprotein ligand associated disorders such as inflammatory or immune system disorders (e.g., inflammatory bowel disease, ulcerative colitis, Crohn's disease, leukocyte adhesion deficiency II syndrome, peritonitis, lung inflammation, asthma, acute appendicitis, septic shock, nephritis, amyloidosis, rheumatoid arthritis, sarcoidosis, scleroderma, lupus, polymyositis, Reiter's syndrome, psoriasis, pelvic inflammatory disease, inflammatory breast disease, orbital inflammatory disease, immune deficiency disorders (e.g., HIV, common variable immunodeficiency, severe combined immunodeficiency), autoimmune disorders, and neurodegenerative diseases (e.g., Alzheimer's disease); hematopoietic or thrombotic disorders (e.g., disseminated intravascular coagulation, anemia, lymphoma, leukemia, neutrophilia, neutropenia, myeloproliferative disorders, thrombocytosis, thrombocytopenia, vonWillebrand disease, and hemophilia); cardiovascular system disorders (e.g., arteriosclerosis, ischemia reperfusion injury, inflammatory heart disease, restenosis, arterial inflammation, vascular wall remodeling, coronary microembolism, congestive heart failure, cardiomyopathy, coronary artery ligation, vascular heart disease, angina, hypertension, myocardial infarction, coronary artery disease, and atherosclerosis); and cellular proliferation, activation, adhesion, growth, differentiation, or migration disorders (e.g., carcinoma, sarcoma, or leukemia; tumor angiogenesis and metastasis; and hematopoietic and/or myeloproliferative disorders)).

In one embodiment, the present invention provides for the use of the SLIC-1 nucleic acid and protein molecules to identify a therapeutic molecule to modulate the activation of cells expressing SLIC-1. In another embodiment, the present invention provides for the use of variants of SLIC-1 nucleic acid and protein molecules (e.g., a dominant-negative SLIC-1 molecule) to modulate cell proliferation, e.g., following novel exogenous gene delivery or gene therapy.

Moreover, the anti-SLIC-1 antibodies of the invention can be used to detect and isolate SLIC-1 proteins, to regulate the bioavailability of SLIC-1 proteins, and to modulate SLIC-1 activity.

A. Screening Assays:

The invention provides a method (also referred to herein as a "screening assay") for identifying modulators, i.e., candidate or test compounds or agents (e.g., peptides, peptidomimetics, small molecules or other drugs) which bind to SLIC-1 proteins, have a stimulatory or inhibitory effect on, for example, SLIC-1 expression or SLIC-1 activity, or have a stimulatory or inhibitory effect on, for example, the expression or activity of SLIC-1 substrate.

In one embodiment, the invention provides assays for screening candidate or test compounds which are substrates of a SLIC-1 protein or polypeptide or biologically active portion thereof. In another embodiment, the invention provides assays for screening candidate or test compounds which bind to or modulate the activity of a SLIC-1 protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a SLIC-1 protein or biologically active portion thereof is contacted with a test compound and the ability of the test compound to modulate SLIC-1 activity is determined. Determining the ability of the test compound to modulate SLIC-1 activity can be accomplished by monitoring, for example, the pattern of protein tyrosine phosphorylation and/or cytoskeletal association of PSGL-1 in a cell which expresses SLIC-1. The cell, for example, can be of mammalian origin, e.g., a hematopoietic cell.

The ability of the test compound to modulate SLIC-1 binding to a substrate or to bind to SLIC-1 can also be determined. Determining the ability of the test compound to modulate SLIC-1 binding to a substrate can be accomplished, for example, by coupling the SLIC-1 substrate with a radioisotope or enzymatic label such that binding of the SLIC-1 substrate to SLIC-1 can be determined by detecting the labeled SLIC-1 substrate in a complex. Alternatively, SLIC-1 could be coupled with a radioisotope or enzymatic label to monitor the ability of a test compound to modulate SLIC-1 binding to a SLIC-1 substrate in a complex. Determining the ability of the test compound to bind SLIC-1 can be accomplished, for example, by coupling the compound with a radioisotope or enzymatic label such that binding of the compound to SLIC-1 can be determined by detecting the labeled SLIC-1 compound in a complex. For example, compounds (e.g., SLIC-1 substrates) can be labeled with $^{125}I$, $^{35}S$, $^{14}C$, or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a SLIC-1 substrate) to interact with SLIC-1 without the labeling of any of the interactants. For example, a microphysiometer can be used to detect the interaction of a compound with SLIC-1 without the labeling of either the compound or the SLIC-1. McConnell, H. M. et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an-indicator of the interaction between a compound and SLIC-1.

In another embodiment, an assay is a cell-based assay comprising contacting a cell expressing a SLIC-1 target molecule (e.g., a SLIC-1 substrate) with a test compound and determining the ability of the test compound to modulate (e.g., stimulate or inhibit) the activity of the SLIC-1 target molecule. Determining the ability of the test compound to modulate the activity of a SLIC-1 target molecule can be accomplished, for example, by determining the ability of the SLIC-1 protein to bind to or interact with the SLIC-1 target molecule.

Determining the ability of the SLIC-1 protein, or a biologically active fragment thereof, to bind to or interact with a SLIC-1 target molecule can be accomplished by one of the methods described above for determining direct binding. In a preferred embodiment, determining the ability of the SLIC-1 protein to bind to or interact with a SLIC-1 target molecule can be accomplished by determining the activity of the target molecule. For example, the activity of the target molecule can be determined by detecting induction of a cellular response (i. e., changes in the tyrosine phosporylation pattern of intracellular proteins; changes in the activity of a MAP kinase or a Ras GTPase; secretion of IL-8), detecting catalytic/enzymatic activity of the target on an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a SLIC-1 protein or biologically active portion thereof is contacted with a test compound and the ability of the test compound to bind to the SLIC-1 protein or biologically active portion thereof is determined. Preferred biologically active portions of the SLIC-1 proteins to be used in assays of the present invention include fragments which participate in interactions with non-SLIC-1 molecules, e.g., fragments comprising an immunoreceptor tyrosine-based activation motif. Binding of the test compound to the SLIC-1 protein can be determined either directly or indirectly as described above. In a preferred embodiment, the assay includes contacting the SLIC-1 protein or biologically active portion thereof with a known compound which binds SLIC-1 to form an assay mixture, contacting the assay mixture with a test compound, and determining the ability of the test compound to interact with a SLIC-1 protein, wherein determining the ability of the test compound to interact with a SLIC-1 protein comprises determining the ability of the test compound to preferentially bind to SLIC-1 or biologically active portion thereof as compared to the known compound.

In another embodiment, the assay is a cell-free assay in which a SLIC-1 protein or biologically active portion thereof is contacted with a test compound and the ability of the test compound to modulate (e.g., stimulate or inhibit) the activity of the SLIC-1 protein or biologically active portion thereof is determined. Determining the ability of the test compound to modulate the activity of a SLIC-1 protein can be accomplished, for example, by determining the ability of the SLIC-1 protein to bind to a SLIC-1 target molecule by one of the methods described above for determining direct binding. Determining the ability of the SLIC-1 protein to bind to a SLIC-1 target molecule can also be accomplished using a technology such as real-time Biomolecular Interaction Analysis (BIA). Sjolander, S. and Urbaniczky, C. (1991) *Anal. Chem.* 63:2338–2345 and Szabo et al. (1995) *Curr. Opin. Struct. Biol.* 5:699–705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a SLIC-1 protein can be accomplished by determining the ability of the SLIC-1 protein to further modulate the activity of a downstream effector of a SLIC-1 target molecule. For example, the activity of the effector molecule on an appropriate target can be determined or the binding of the effector to an appropriate target can be determined as previously described.

In yet another embodiment, the cell-free assay involves contacting a SLIC-1 protein or biologically active portion thereof with a known compound which binds the SLIC-1 protein to form an assay mixture, contacting the assay mixture with a test compound, and determining the ability of the test compound to interact with the SLIC-1 protein, wherein determining the ability of the test compound to interact with the SLIC-1 protein comprises determining the ability of the SLIC-1 protein to preferentially bind to or modulate the activity of a SLIC-1 target molecule.

In more than one embodiment of the above assay methods of the present invention, it may be desirable to immobilize either SLIC-1 or its target molecule to facilitate separation of complexed from uncomplexed forms of one or both of the proteins, as well as to accommodate automation of the assay. Binding of a test compound to a SLIC-1 protein, or interaction of a SLIC-1 protein with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/SLIC-1 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or SLIC-1 protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of SLIC-1 binding or activity determined using standard techniques.

Other techniques for immobilizing proteins on matrices can also be used in the screening assays of the invention. For example, either a SLIC-1 protein or a SLIC-1 target molecule can be immobilized utilizing conjugation of biotin and streptavidin. Biotinylated SLIC-1 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with SLIC-1 protein or target molecules but which do not interfere with binding of the SLIC-1 protein to its target molecule can be derivatized to the wells of the plate, and unbound target or SLIC-1 protein trapped in the wells by antibody conjugation. Methods for detecting such complexes, in addition to those described above for the GST-immobilized complexes, include immunodetection of complexes using antibodies reactive with the SLIC-1 protein or target molecule, as well as enzyme-linked assays which rely on detecting an enzymatic activity associated with the SLIC-1 protein or target molecule.

In another embodiment, modulators of SLIC-1 expression are identified in a method wherein a cell is contacted with a candidate compound and the expression of SLIC-1 mRNA or protein in the cell is determined. The level of expression of SLIC-1 mRNA or protein in the presence of the candidate compound is compared to the level of expression of SLIC-1 mRNA or protein in the absence of the candidate compound. The candidate compound can then be identified as a modulator of SLIC-1 expression based on this comparison. For example, when expression of SLIC-1 mRNA or protein is greater (statistically significantly greater) in the presence of the candidate compound than in its absence, the candidate compound is identified as a stimulator of SLIC-1 mRNA or protein expression. Alternatively, when expression of SLIC-1 mRNA or protein is less (statistically significantly less) in the presence of the candidate compound than in its absence, the candidate compound is identified as an inhibitor of SLIC-1 mRNA or protein expression. The level of SLIC-1 mRNA or protein expression in the cells can be determined by methods described herein for detecting SLIC-1 mRNA or protein.

In yet another aspect of the invention, the SLIC-1 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with SLIC-1 ("SLIC-1-binding proteins" or "SLIC-1-bp") and are involved in SLIC-1 activity. Such SLIC-1-binding proteins are also likely to be involved in the propagation of signals by the SLIC-1 proteins or SLIC-1 targets as, for example, downstream elements of a SLIC-1-mediated signaling pathway. Alternatively, such SLIC-1-binding proteins are likely to be SLIC-1 inhibitors.

The two-hybrid system is based on the modular nature of most transcription factors, which consist of separable DNA-binding and activation domains. Briefly, the assay utilizes two different DNA constructs. In one construct, the gene that codes for a SLIC-1 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a SLIC-1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the SLIC-1 protein.

In another aspect, the invention pertains to a combination of two or more of the assays described herein. For example, a modulating agent can be identified using a cell-based or a cell free assay, and the ability of the agent to modulate the activity of a SLIC-1 protein can be confirmed in vivo, e.g., in an animal such as an animal model for inflammation.

This invention further pertains to novel agents identified by the above-described screening assays. Accordingly, it is within the scope of this invention to further use an agent identified as described herein in an appropriate animal model. For example, an agent identified as described herein (e.g., a SLIC-1 modulating agent, an antisense SLIC-1 nucleic acid molecule, a SLIC-1-specific antibody, or a SLIC-1-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

B. Detection Assays

Portions or fragments of the cDNA sequences identified herein (and the corresponding complete gene sequences) can be used in numerous ways as polynucleotide reagents For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the SLIC-1 nucleotide sequences, described herein, can be used to map the location of the SLIC-1 genes on a chromosome. The mapping of the SLIC-1 sequences to chromosomes is an important first step in correlating these sequences with genes associated with disease.

Briefly, SLIC-1 genes can be mapped to chromosomes by preparing PCR primers (preferably 15–25 bp in length) from the SLIC-1 nucleotide sequences. Computer analysis of the SLIC-1 sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the SLIC-1 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) Science 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the SLIC-1 nucleotide sequences to design oligonucleotide primers, sublocalization can be achieved with panels of fragments from specific chromosomes. Other mapping strategies which can similarly be used to map a SLIC-1 sequence to its chromosome include in situ hybridization (described in Fan, Y. et al. (1990) Proc. Natl. Acad. Sci. USA, 87:6223–27), pre-screening with labeled flow-sorted chromosomes, and preselection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping. The human SLIC-1 gene has been localized to chromosome 16.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) Nature, 325:783–787.

Moreover, differences in the DNA sequences between individuals affected and unaffected with a disease associated with the SLIC-1 gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The SLIC-1 sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the SLIC-1 nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The SLIC-1 nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of the SLIC-1 gene can comfortably provide positive individual identification with a panel of perhaps 10 to 1,000 primers which each yield a noncoding amplified sequence of 100 bases. If predicted coding sequences, such as those in SEQ ID NO:1 are used, a more appropriate number of primers for positive individual identification would be 500–2,000.

If a panel of reagents from SLIC-1 nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of SLIC-1 Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (ie. another DNA sequence that is unique to a particular individual). As mentioned above, actual base sequence information can be used for identification as an accurate alternative to patterns formed by restriction enzyme generated fragments. Sequences targeted to noncoding regions of the SLIC-1 gene are particularly appropriate for this use as greater numbers of polymorphisms occur in the noncoding regions, making it easier to differentiate individuals using this technique. Examples of polynucleotide reagents include the SLIC-1 nucleotide sequences or portions thereof, e.g., fragments derived from SEQ ID NO:1 or the noncoding regions of the SLIC-1 gene having a length of at least 20 bases, preferably at least 30 bases.

The SLIC-1 nucleotide sequences described herein can further be used to provide polynucleotide reagents, e.g., labeled or labelable probes which can be used in, for example, an in situ hybridization technique, to identify a specific tissue, e.g., hematopoietic and/or lymphoid tissue. This can be very useful in cases where a forensic pathologist is presented with a tissue of unknown origin. Panels of such SLIC-1 probes can be used to identify tissue by species and/or by organ type.

In a similar fashion, these reagents, e.g., SLIC-1 primers or probes can be used to screen tissue culture for contamination (i. e. screen for the presence of a mixture of different types of cells in a culture).

C. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining SLIC-1 protein and/or nucleic acid expression as well as SLIC-1 activity, in the context of a biological sample (e.g., blood, serum, cells, tissue) to thereby determine whether an individual is afflicted with a disease or disorder, or is at risk of developing a disorder, associated with aberrant or unwanted SLIC-1 expression or activity. The invention also provides for prognostic (or predictive) assays for determining whether an individual is at risk of developing a disorder associated with SLIC-1 protein, nucleic acid expression or activity. For example, mutations in a SLIC-1 gene can be assayed in a biological sample. Such assays can be used for prognostic or predictive purpose to thereby phophylactically treat an individual prior to the onset of a disorder characterized by or associated with SLIC-1 protein, nucleic acid expression or activity.

Another aspect of the invention pertains to monitoring the influence of agents (e.g., drugs, compounds) on the expression or activity of SLIC-1 in clinical trials.

These and other agents are described in further detail in the following sections.

1. Diagnostic Assays

An exemplary method for detecting the presence or absence of SLIC-1 protein or nucleic acid in a biological sample involves obtaining a biological sample from a test subject and contacting the biological sample with a compound or an agent capable of detecting SLIC-1 protein or nucleic acid (e.g., mRNA, or genomic DNA) that encodes SLIC-1 protein such that the presence of SLIC-1 protein or nucleic acid is detected in the biological sample. A preferred agent for detecting SLIC-1 mRNA or genomic DNA is a labeled nucleic acid probe capable of hybridizing to SLIC-1 mRNA or genomic DNA. The nucleic acid probe can be, for example, the SLIC-1 nucleic acid set forth in SEQ ID NO:1, or a portion thereof, such as an oligonucleotide of at least 15, 30, 50, 100, 250 or 500 nucleotides in length and sufficient to specifically hybridize under stringent conditions to SLIC-1 mRNA or genomic DNA. Other suitable probes for use in the diagnostic assays of the invention are described herein.

A preferred agent for detecting SLIC-1 protein is an antibody capable of binding to SLIC-1 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect SLIC-1 mRNA, protein, or genomic DNA in a biological sample in vitro as well as in vivo. For example, in vitro techniques for detection of SLIC-1 mRNA include Northern hybridizations and in situ hybridizations. In vitro techniques for detection of SLIC-1 protein include enzyme linked immunosorbent assays (ELISAs), Western blots, immunoprecipitations and immunofluorescence. In vitro techniques for detection of SLIC-1 genomic DNA include Southern hybridizations. Furthermore, in vivo techniques for detection of SLIC-1 protein include introducing into a subject a labeled anti-SLIC-1 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting SLIC-1 protein, mRNA, or genomic DNA, such that the presence of SLIC-1 protein, mRNA or genomic DNA is detected in the biological sample, and comparing the presence of SLIC-1 protein, mRNA or genomic DNA in the control sample with the presence of SLIC-1 protein, mRNA or genomic DNA in the test sample.

The invention also encompasses kits for detecting the presence of SLIC-1 in a biological sample. For example, the kit can comprise a labeled compound or agent capable of detecting SLIC-1 protein or mRNA in a biological sample; means for determining the amount of SLIC-1 in the sample; and means for comparing the amount of SLIC-1 in the sample with a standard. The compound or agent can be packaged in a suitable container. The kit can further comprise instructions for using the kit to detect SLIC-1 protein or nucleic acid.

2. Prognostic Assays

The diagnostic methods described herein can furthermore be utilized to identify subjects having or at risk of developing a disease or disorder associated with aberrant or unwanted SLIC-1 expression or activity. As used herein, the term "aberrant" includes a SLIC-1 expression or activity which deviates from the wild type SLIC-1 expression or activity. Aberrant expression or activity includes increased or decreased expression or activity, as well as expression or activity which does not follow the wild type developmental pattern of expression or the subcellular pattern of expression. For example, aberrant SLIC-1 expression or activity is intended to include the cases in which a mutation in the SLIC-1 gene causes the SLIC-1 gene to be under-expressed or over-expressed and situations in which such mutations result in a non-functional SLIC-1 protein or a protein which does not function in a wild-type fashion, e.g., a protein which does not interact with a SLIC-1 substrate, or one which interacts with a non-SLIC-1 substrate. As used herein, the term "unwanted" includes an unwanted phenomenon involved in a biological response such as cellular proliferation. For example, the term unwanted includes a SLIC-1 expression or activity which is undesirable in a subject.

The assays described herein, such as the preceding diagnostic assays or the following assays, can be utilized to identify a subject having or at risk of developing a disorder associated with a misregulation in SLIC-1 protein activity or nucleic acid expression, such as an inflammatory or immune system disorder; a cardiovascular disorder; a cellular proliferation, activation, adhesion, growth, differentiation, or migration disorder; or a hematopoietic or thrombotic disorder. Alternatively, the prognostic assays can be utilized to identify a subject having or at risk for developing a disorder associated with a misregulation in SLIC-1 protein activity or nucleic acid expression, such as an inflammatory or immune system disorder; a cardiovascular disorder; a cellular proliferation, activation, adhesion, growth, differentiation, or migration disorder; or a hematopoietic or thrombotic disorder. Thus, the present invention provides a method for identifying a disease or disorder associated with aberrant or unwanted SLIC-1 expression or activity in which a test sample is obtained from a subject and SLIC-1 protein or nucleic acid (e.g, mRNA or genomic DNA) is detected, wherein the presence of SLIC-1 protein or nucleic acid is diagnostic for a subject having or at risk of developing a disease or disorder associated with aberrant or unwanted SLIC-1 expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted SLIC-1 expression or activity. For example, such methods can be used to determine whether a subject can be effectively treated with an agent for an inflammatory or immune system disorder; a cardiovascular disorder; a cellular proliferation, activation, adhesion, growth, differentiation, or migration disorder; or a hematopoietic or thrombotic disorder. Thus, the present invention provides methods for determining whether a subject can be effectively treated with an agent for a disorder associated with aberrant or unwanted SLIC-1 expression or activity in which a test sample is obtained and SLIC-1 protein or nucleic acid expression or activity is detected (e.g., wherein the abundance of SLIC-1 protein or nucleic acid expression or activity is diagnostic for a subject that can be administered the agent to treat a disorder associated with aberrant or unwanted SLIC-1 expression or activity).

The methods of the invention can also be used to detect genetic alterations in a SLIC-1 gene, thereby determining if a subject with the altered gene is at risk for a disorder characterized by misregulation in SLIC-1 protein activity or nucleic acid expression, such as an inflammatory or immune system disorder; a cardiovascular disorder; a cellular proliferation, activation, adhesion, growth, differentiation, or migration disorder; or a hematopoietic or thrombotic disorder. In preferred embodiments, the methods include detecting, in a sample of cells from the subject, the presence or absence of a genetic alteration characterized by at least one of an alteration affecting the integrity of a gene encoding a SLIC-1-protein, or the mis-expression of the SLIC-1 gene. For example, such genetic alterations can be detected by ascertaining the existence of at least one of 1) a deletion of one or more nucleotides from a SLIC-1 gene; 2) an addition of one or more nucleotides to a SLIC-1 gene; 3) a substitution of one or more nucleotides of a SLIC-1 gene, 4) a chromosomal rearrangement of a SLIC-1 gene; 5) an alteration in the level of a messenger RNA transcript of a SLIC-1 gene, 6) aberrant modification of a SLIC-1 gene, such as of the methylation pattern of the genomic DNA, 7) the presence of a non-wild type splicing pattern of a messenger RNA transcript of a SLIC-1 gene, 8) a non-wild type level of a SLIC-1-protein, 9) allelic loss of a SLIC-1 gene, and 10) inappropriate post-translational modification of a SLIC-1-protein. As described herein, there are a large number of assays known in the art which can be used for detecting alterations in a SLIC-1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the SLIC-1-gene (see Abravaya et al. (1995) *Nucleic Acids Res.* 23:675–682). This method can include the steps of collecting a sample of cells from a subject, isolating nucleic acid (e.g., genomic, mRNA or both) from the cells of the sample, contacting the nucleic acid sample with one or more primers which specifically hybridize to a SLIC-1 gene under conditions such that hybridization and amplification of the SLIC-1-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a SLIC-1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in SLIC-1 can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244–255; Kozal, M. J. et al. (1996) *Nature Medicine* 2: 753–759). For example, genetic mutations in SLIC-1 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the SLIC-1 gene and detect mutations by comparing the sequence of the sample SLIC-1 with the corresponding wild-type (control) sequence. Examples of sequencing reactions include those based on techniques developed by Maxam and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the SLIC-1 gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type SLIC-1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl Acad Sci USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in SLIC-1 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a SLIC-1 sequence, e.g, a wild-type SLIC-1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in SLIC-1 genes. For example, single strand conformation polymorphism (SSCP) may be used to detect differences in electrophoretic mobility between mutant and wild type nucleic acids (Orita et al. (1989) *Proc Natl. Acad. Sci USA*: 86:2766, see also Cotton (1993) *Mutat. Res.* 285:125–144; and Hayashi (1992) *Genet. Anal. Tech. Appl.* 9:73–79). Single-stranded DNA fragments of sample and control SLIC-1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a SLIC-1 gene.

Furthermore, any cell type or tissue in which SLIC-1 is expressed may be utilized in the prognostic assays described herein.

3. Monitoring of Effects During Clinical Trials

Monitoring the influence of agents (e.g., drugs) on the expression or activity of a SLIC-1 protein (e.g., the modulation of inflammatory and/or PSGL-1 signaling mechanisms, PSGL-1 cytoskeletal association, or cell adhesion) can be applied not only in basic drug screening, but also in clinical trials. For example, the effectiveness of an agent determined by a screening assay as described herein to increase SLIC-1 gene expression, protein levels, or upregulate SLIC-1 activity, can be monitored in clinical trials of subjects exhibiting decreased SLIC-1 gene expression, protein levels, or downregulated SLIC-1 activity. Alternatively, the effectiveness of an agent determined by a screening assay to decrease SLIC-1 gene expression, protein levels, or downregulate SLIC-1 activity, can be monitored in clinical trials of subjects exhibiting increased SLIC-1 gene expression, protein levels, or upregulated SLIC-1 activity. In such clinical trials, the expression or activity of a SLIC-1 gene, and preferably, other genes that have been implicated in, for example, a SLIC-1-associated disorder can be used as a "read out" or markers of the phenotype of a particular cell.

For example, and not by way of limitation, genes, including SLIC-1, that are modulated in cells by treatment with an agent (e.g., compound, drug or small molecule) which modulates SLIC-1 activity (e.g., identified in a screening assay as described herein) can be identified. Thus, to study the effect of agents on SLIC-1-associated disorders (e.g., disorders characterized by deregulated P-selectin glycoprotein ligand signaling mechanisms and/or cellular adhesion), for example, in a clinical trial, cells can be isolated and RNA prepared and analyzed for the levels of expression of SLIC-1 and other genes implicated in the SLIC-1-associated disorder, respectively. The levels of gene expression (e.g., a gene expression pattern) can be quantified by northern blot analysis or RT-PCR, as described herein, or alternatively by measuring the amount of protein produced, by one of the methods as described herein, or by measuring the levels of activity of SLIC-1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a SLIC-1 protein, mRNA, or genomic DNA in the preadministration sample; (iii) obtaining one or more post-administration samples from the subject; (iv) detecting the level of expression or activity of the SLIC-1 protein, mRNA, or genomic DNA in the post-administration samples; (v) comparing the level of expression or activity of the SLIC-1 protein, mRNA, or genomic DNA in the pre-administration sample with the SLIC-1 protein, mRNA, or genomic DNA in the post administration sample or samples; and (vi) altering the administration of the agent to the subject accordingly. For example, increased administration of the agent may be desirable to increase the expression or activity of SLIC-1 to higher levels than detected, ie., to increase the effectiveness of the agent. Alternatively, decreased administration of the agent may be desirable to decrease expression or activity of SLIC-1 to lower levels than detected, i.e. to decrease the effectiveness of the agent. According to such an embodiment, SLIC-1 expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant or unwanted SLIC-1 expression or activity, e.g an inflammatory or immune system disorder; a cardiovascular disorder; a cellular proliferation, activation, adhesion, growth, differentiation, or migration disorder; or a hematopoietic or thrombotic disorder. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the SLIC-1 molecules of the present invention or SLIC-1 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant or unwanted SLIC-1 expression or activity, by administering to the subject a SLIC-1 or an agent which modulates SLIC-1 expression or at least one SLIC-1 activity. Subjects at risk for a disease which is caused or contributed to by aberrant or unwanted SLIC-1 expression or activity can be identified by, for example, any or a combination of diagnostic or prognostic assays as described herein. Administration of a prophylactic agent can occur prior to the manifestation of symptoms characteristic of the SLIC-1 aberrancy, such that a disease or disorder is prevented or, alternatively, delayed in its progression. Depending on the type of SLIC-1 aberrancy, for example, a SLIC-1, SLIC-1 agonist or SLIC-1 antagonist agent can be used for treating the subject. The appropriate agent can be determined based on screening assays described herein.

2. Therapeutic Methods

Another aspect of the invention pertains to methods of modulating SLIC-1 expression or activity for therapeutic purposes. Accordingly, in an exemplary embodiment, the modulatory method of the invention involves contacting a cell with a SLIC-1 or agent that modulates one or more of the activities of SLIC-1 protein activity associated with the cell. An agent that modulates SLIC-1 protein activity can be an agent as described herein, such as a nucleic acid or a protein, a naturally-occurring target molecule of a SLIC-1 protein (e.g., a SLIC-1 substrate), a SLIC-1 antibody, a SLIC-1 agonist or antagonist, a peptidomimetic of a SLIC-1 agonist or antagonist, or other small molecule. In one embodiment, the agent stimulates one or more SLIC-1 activities. Examples of such stimulatory agents include active SLIC-1 protein and a nucleic acid molecule encoding SLIC-1 that has been introduced into the cell. In another embodiment, the agent inhibits one or more SLIC-1 activities. Examples of such inhibitory agents include antisense SLIC-1 nucleic acid molecules, anti-SLIC-1 antibodies, and SLIC-1 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a SLIC-1 protein or nucleic acid molecule. In one embodiment, the method involves administering an agent (e.g., an agent identified by a screening assay described herein), or combination of agents that modulates (e.g., upregulates or downregulates) SLIC-1 expression or activity. In another embodiment, the method involves administering a SLIC-1 protein or nucleic acid molecule as therapy to compensate for reduced, aberrant, or unwanted SLIC-1 expression or activity.

Stimulation of SLIC-1 activity is desirable in situations in which SLIC-1 is abnormally downregulated and/or in which increased SLIC-1 activity is likely to have a beneficial effect. Likewise, inhibition of SLIC-1 activity is desirable in situations in which SLIC-1 is abnormally upregulated and/or in which decreased SLIC-1 activity is likely to have a beneficial effect.

3. Pharmacogenomics

The SLIC-1 molecules of the present invention, as well as agents, or modulators which have a stimulatory or inhibitory effect on SLIC-1 activity (e.g., SLIC-1 gene expression) as identified by a screening assay described herein can be administered to individuals to treat (prophylactically or therapeutically) SLIC-1-associated disorders (e.g., inflammatory or immune system disorders; cardiovascular disorders; cellular proliferation, activation, adhesion, growth, differentiation, or migration disorders; hematopoietic or thrombotic disorders) associated with aberrant or unwanted SLIC-1 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a SLIC-1 molecule or SLIC-1 modulator as well as tailoring the dosage and/or therapeutic regimen of treatment with a SLIC-1 molecule or SLIC-1 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10–11): 983–985 and Linder, M. W. et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a SLIC-1 protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a SLIC-1 molecule or SLIC-1 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a SLIC-1 molecule or SLIC-1 modulator, such as a modulator identified by one of the exemplary screening assays described herein.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Yeast-Two-Hybrid Screen Using the Cytoplasmic Domain OF PSGL-1

A yeast-two-hybrid screen (Gyuris et al. 1993, Cell 75:791–803) was performed to identify proteins that interact with the cytoplasmic domain of human PSGL-1 (PSLcyt).

A. Construction of the Bait Plasmid

The cytoplasmic domain of PSGL-1 was amplified via PCR using full length human PSGL-1 cDNA (Sako et al.

1993, Cell 75:1179–1186) as a template. The following PCR primers were used which introduced EcoRI and BamHI restriction sites for subcloning:

```
                                              (SEQ ID NO:3)
PSLCY5 5'-ATACTGAATTCCGCCTCTCCCGCAAGGGCCACAT-3'
                                              (SEQ ID NO:4)
PSLCY3 5'-ATACAGGATCCAGAGTGAGCTAACGGAGGAAAG-3'
```

A 240 bp product corresponding to the cytoplasmic domain of PSGL-1 (PSLcyt) was amplified under the PCR conditions of 30 cycles of 94° C. for 1 minute, 60° C. for 1 minute, and 72° C. for 1 minute. PCR reagents were purchased from Perkin Elmer.

The bait plasmid pEG202 was digested with EcoRI and BamHI, treated with calf intestinal phosphatase (New England Biolabs), and purified using a phenol/chloroform extraction followed by precipitation in ethanol. The PSLcyt PCR product was digested with EcoRI and BamHI, purified, and ligated with bait plasmid pEG202. This construct enables the expression a novel fusion protein consisting of the cytoplasmic domain of PSGL-1 fused to the carboxy terminus of the LexA DNA binding protein.

XL1Blue E.coli bacteria cells (Stratagene) were transformed with the ligated plasmids via electroporation in 1 mm cuvettes (BIORAD) using a Gene Pulser (BIORAD). Plasmid minipreps were screened for the insert by EcoRI/BamHI restriction digestion and size fractionation of the fragments by electrophoresis on 1% agarose gels stained with ethidium bromide. Upon identification of plasmids containing an insert of the correct size, QIAGEN Plasmid Maxi kits were used for large scale plasmid preparation. In addition, DNA sequence analysis was performed to confirm the correct sequence for PSLcyt. The sequence of the introduced DNA fragment was identical with the sequence of PSGL-1 over nucleotides 1057 to 1277 (Sako et al. 1993, Cell 75:1179–1186).

B. Interactor Screen With a U937 cDNA Library

Yeast strain EGY48–34 was transformed with the LexA-PSLcyt bait plasmid and Western blotting with an anti-LexA antibody (Invitrogen) was performed to confirm expression of the LexA-PSLcyt fusion protein. A specific band was detected at the expected size of approximately 32 kD.

To assess for transcriptional activity of the LexA-PSLcyt bait protein, EGY48 yeast carrying the pSH18–34 lacZ reporter plasmid were transformed with the pEG202-PSLcyt bait plasmid and empty vector pJG4–5 for the prey protein. Background levels were found to be normal when the transformed yeast were tested for non-specific activation of the Leu2 and lacZ reporter genes.

The amplified material of a U937 cell cDNA library in the vector pJG4–5 (prey) was used to transform EGY48 yeast cells carrying the LexA-PSLcyt bait protein. For the transformation, yeast cultures were grown to an OD600 of approximately 0.5 from fresh overnight cultures. The yeast were resuspended in 1.5 ml 1×TE buffer/0.1 M lithium acetate after a wash in sterile water. Thirty transformation reactions comprising 50 μL yeast suspension, 1 μg library DNA and 50 μg heat-denatured carrier DNA were performed. After incubation at 30° C. for 30 minutes in 300 μL 40% PEG4000, the reactions were heat shocked at 42° C. for 10 minutes in the presence of 10% DMSO. The transformation reactions were plated on 243×243 mm plates deficient for the amino acids uracil, histidine and tryptophan (CMD-U-H-W medium, Genetics Institute) to allow for selective growth of yeast carrying both the bait and the library plasmid. Growing yeast were collected from the plates and stored as glycerol stocks at −80° C.

The re-plating efficiency of the yeast glycerol stocks was determined and an interactor screen was performed by plating 10 million colony forming units (CFU) of yeast on plates containing X-gal and galactose, but lacking the amino acids uracil, histidine, tryptophan and leucine (CMG/R-U-H-W-L+X-Gal medium, Genetics Institute). After 3–4 overnight incubations blue colonies from these plates were picked and twice replated on CMG/R-U-H-W-L+X-Gal master plates. Fifty two candidate colonies from these plates were transferred to four different tester plates, CMD-U-H-W+X-Gal, CMG/R-U-H-W-L, CMD-U-H-W-L and CMG/R-3+X-Gal, to further test specific activation.

Clones inducing specific activation of the Leu2 and lacZ reporter genes are expected to form white colonies on CMD-U-H-W+X-Gal and CMG/R-U-H-W-L plates. No growth or very weak growth is expected on CMD-U-H-W-L plates, and blue CFUs are expected on CMG/R-3+X-Gal plates. The appearance of each candidate clone following plating on the 4 tester plates was used to select those clones which showed an overall specific induction pattern compared to other clones showing less specificity.

C. Analysis of Candidate Positive Clones

The interactor screen resulted in the identification of 11 clones which appeared to interact specifically with the PSLcyt bait. Plasmid DNA was extracted from these yeast cells and used to transform KC8 bacteria (CLONTECH). Selective growth of transformed bacteria on CAA medium in the presence of ampicillin was observed due to the ampicillin resistance gene and the TRP1 gene on the pJG4–5 library plasmid. Minipreps from transformed bacteria were screened by EcoRI/XhoI restriction digestion to determine the size of the DNA insert and to identify possible new restriction sites. For each of the 11 initial interacting clones identified in the yeast-two hybrid system, the plasmid DNA from one KC8 clone was subjected to partial DNA sequence analysis of the cDNA insert. Clones with identical restriction digestion patterns and identical DNA sequences were grouped together for further studies. Four different groups were formed. For each group of clones, with matching restriction digestion patterns and DNA sequences, one clone was used to retransform yeast with PSLcyt as a bait protein. Using this method, the specificity of the bait-library protein (prey) interaction was retested in the 4-tester plate assay. In this assay two clones, designated 2.8.3 and 8.1.1, were identified to interact specifically with the PSLcyt bait protein.

Example 2

Isolation of Full Length SLIC-1 cDNA from a U937 Cell Library

The full length form of SLIC-1 cDNA was cloned from a bacteria phage, lambda ZAPII random primed U937 cell cDNA library (Genetics Institute) by conventional library screening methods. Approximately 1×10$^6$ pfu of the library were plated on NZCYM plates with top agarose. Duplicate filter lifts using Duralose-UV membranes (Stratagene) were performed. Prehybridization and hybridization of the filters was performed in 5×SSC, 533 Denhardt's solution, 0.1% SDS and 50 μg/mL carrier RNA (SIGMA) at 65° C.

To generate a probe for library screening, the pJG4–5 plasmid containing the partial cDNA clone 8.1.1 isolated from the yeast-two-hybrid screen was sequentially digested with ApaI and EcoRI. The resulting fragment of approximately 0.5 kb was isolated using a QIAXII Agarose Gel Extraction Kit (QIAGEN). Random priming with this material was performed for 1 hour at room temperature in the presence of $^{32}$P-dATP and $^{32}$P-CTP (Amersham), 6-mer random primers (Genetics Institute) and Klenow Large Fragment (New England Biolabs). The products were purified using a Sephadex G-50 column (Pharmacia). The filters were hybridized with the $^{32}$P-labeled EcoRI/ApaI fragment probe, and washed 4 times in 0.2×SSC/0.1% SDS. Autoradiographs of the filters were developed after overnight storage at −80° C. Based on the autoradiography results, 12 positive plaques were isolated for further characterization. These phage clones were rescreened according to the method described above resulting in the selection of three positive clones.

The cDNA inserts of the three positive clones were subcloned into pBluescript by consecutive coincubation of the phage of interest with BB4–7 E. coli and XL-1 Blue E. coli in the presence of ExAssist helper phage (Stratagene). The three clones were further analyzed by restriction digests with EcoRI, NotI and BssHI (New England Biolabs), as well as partial DNA sequencing. One clone, designated clone Uran-5, contained an initiation codon and an additional 5' open reading frame consistent with that of the 8.1.1 partial cDNA clone originally identified from the yeast-two-hybrid screen. The complete DNA sequence of the clone Uran-5 was determined and found to contain an open reading frame termed human "SLIC-1."

Accordingly, the invention is based, at least in part, on the discovery of a human gene encoding a novel protein, referred to herein as SLIC-1. The nucleotide sequence encoding the human SLIC-1 protein is shown in FIGS. 1A and 1B and is set forth as SEQ ID NO:1. The protein encoded by this nucleic acid comprises about 316 amino acids and has the amino acid sequence shown in FIGS. 1A and 1B and set forth as SEQ ID NO:2.

Tissue Distribution of SLIC-1 mRNA

Northern blot analysis indicates that human SLIC-1 mRNA is expressed only in cells of hematopoietic origin.

Example 3

Expression of SLIC-1 in COS Cells

This example describes the transient expression of SLIC-1 cDNA was in COS cells. An 1.5 kb Sal DNA fragment, containing the entire SLIC-1 coding region within the Uran-5 cDNA clone, was ligated into the Sal I site in the polylinker region of the mammalian expression vector pEDΔC. The presence and the correct orientation of the DNA insert was confirmed, and the resulting plasmid was designated pED.Uran-5.

COS cells were cultured in 10 cm tissue culture dishes (Corning) to approximately 90% confluency in DME with 10% heat-inactivated Fetal Bovine Serum (SIGMA), Glutamine, and Penicillin/Streptomycin (Gibco). COS cell transfection was performed under standard incubation conditions with 8 µg/dish of plasmid pED.Uran-5 precomplexed with lipofectamine (Gibco) for 45 minutes at room temperature in Opti-MEM (Gibco). On the following day the cells were lysed. The plates were rinsed with PBS-CMF and lysed in 1 mL/plate of cold lysis buffer (25 mM Tris-HCl, pH 8.0, 125 mM NaCl, 1 mM MgCl$_2$, 1% Triton-X). Protease inhibitors (Complete mini tablets, Boehringer Mannheim) were included in the lysis buffer at the recommended concentration. After 30 minutes of lysis on ice, the lysate was cleared by centrifugation at maximum speed for 15 minutes in a refrigerated table top centrifuge. The supernatant was then boiled in 2× reducing sample buffer for 5 minutes, and various volumes of the sample were electrophoresed on 4–20% Tris-Glycine SDS Gels (Novex). The samples were electroblotted onto nitrocellulose membranes (Novex) and Western blotting was performed for the detection of SLIC-1.

The nitrocellulose membranes were blocked at 4° C. overnight in 3% BSA (SIGMA) in Tris Buffered Saline (TBS) with 0.1% Tween-20. The membranes were washed for 7 minutes in TBS-0.1% Tween, and then incubated for 1 hour in a 1:2500 dilution of affinity-purified rabbit anti-SLIC-1 polyclonal antibodies (Research Genetics, Inc.). These antibodies were generated by immunizing rabbits with a polypeptide antigen having the amino acid sequence QERLEESQLRRPTPR (SEQ ID NO:5) conjugated to KLH. The membranes were washed three times in TBS-0.1% Tween, incubated for 1 hour with a secondary antibody to detect rabbit immunoglobulin, and developed using the ECL Western Blotting Detection System (Amersham). Mock transfections and Western blot analysis using unrelated purified polyclonal rabbit IgG (Serotec) were performed in parallel as controls. The results of this analysis are shown in FIG. 2. The SLIC-1 protein exhibits an apparent molecular weight of approximately 45 kD by SDS-PAGE analysis.

Example 4

Interaction of SLIC-1 with PSGL-1 in COS Cells

A. Generation of T7-SLIC-1 Fusion Protein Constructs

A DNA construct that allows the expression of full length SLIC-1 as a fusion protein with a T7 protein tag was generated as follows. A mutated primer for the 5' sequence of SLIC-1 was designed to introduce a T7 tag directly upstream of the initiation codon of SLIC-1 in vector pED.Uran-5 by PCR. The T7 tag encodes the amino acid sequence MASMTGGQQMG (SEQ ID NO:6). The PCR reaction generated a product of approximately 380 bp, spanning the N-terminal end of SLIC-1 beyond an AscI restriction site. A 5' SaiI site and this AscI site were used to replace the original N-terminal end of SLIC-1 in pED.Uran-5 with the PCR product containing the T7 tag. The resulting vector was designated pED.T7Uran-5 and encodes all 316 amino acids of SLIC-1. The pED.T7Uran-5 vector was further used to create three truncated forms of SLIC-1 as follows. The vector pED.T7U5AA226 encodes for the first 226 amino acids of SLIC-1, and was generated by restriction digestion of pED.T7Uran-5 with NotI and AscI and ligation of the plasmid with a NotI/XbaI linker that also comprises a Stop codon to terminate transcription. A similar approach was used to create pED.T7U5AA160, a 160 amino acid short form of SLIC-1 that was generated by restriction digestion of pED.T7Uran-5 with AscI and XbaI and ligation with an appropriate linker. The vector PED.T7U5AA88 was generated by PCR using the original 5' primer for pED.T7Uran-5 and a newly designed 3' primer which introduced a Stop codon and an additional XbaI site after amino acid residue 88 in SLIC-1. The XbaI and SaiI sites in pED.T7Uran-5 were then used to replace the sequence for full length SLIC-1 with this truncated form.

All oligonucleotides were generated at Genetics Institute (Oligonucleotide Synthesis Group), and PCR reagents were purchased from Perkin Elmer. The PCR reactions were performed in a Perkin Elmer DNA Thermal Cycler under the conditions of 25 cycles of incubation at 94° C. for 1 minute, 45° C. for 1 minute and 72° C. for 3 minutes, followed by a final extension step at 72° C. for 7 minutes. The reagents used in the restriction digestion reactions and the ligation reactions were purchased from New England Biolabs, except for additional dATP from Perkin Elmer. All fragments were isolated from agarose gels and purified with a QIAEXII kit (QIAGEN) after incubation with the restriction enzymes. The oligonucleotide linkers were annealed in 20 mM Tris, pH 8, 1 mM MgCl$_2$ and 20 mM NaCl. The ligation reactions were carried out overnight at 16° C. The plasmids were amplified in HB101 cells (BIO-RAD) and isolated from bacteria with plasmid purification kits from QIAGEN according to the manufacturer's instructions. Restriction digests with appropriate restriction enzymes were carried out to confirm proper amplification of the DNA constructs.

B. Transient Overexpression of SLIC-1 and PSGL-1 in COS Cells and Co-immunoprecipitation Using Anti-PSGL-1 Antibodies COS cells were transfected with T7-tagged forms of SLIC-1 as described in Example 3. Vector pMT-PL85A (Genetics Institute) was included in a subset of samples to transiently overexpress the full length form of human PSGL-1. Cell lysis was carried out as described above in 900 μL/dish of lysis buffer consisting of 20 mM Tris-HCl, pH 7.4, 137 mM NaCl, 0.05% Triton-X and protease inhibitors (Hildt, E and Oess, S J 1999 J. Exp. Med. 189(11): 1707–1714). A small volume of cleared cell lysate was used for Western Blotting to detect overexpressed protein in the whole cell lysate and for spectrophotometric measurement of the protein content. A volume of 300 μL of each lysate was used for co-immunoprecipitation studies with either 2.5 μg of biotinylated monoclonal mouse anti-PSGL-1 antibody (antibody 2G3, Genetics Institute) or a biotinylated control antibody (SIGMA). The samples were agitated at 4° C. for 5 hours, and immuncomplexes were precipitated with streptavidin agarose beads (Pierce) under the same conditions for 1 hour. Based on a protocol by Hildt and Oess (supra), the streptavidin agarose beads were washed four times in 0.5 M LiCl/0.1 M Tris HCl, pH 7.4 and 2 times in 0.01M Tris HCl, pH 7.4. The beads were then boiled in 2× reducing sample buffer for 5 minutes, and the samples were electrophoresed and electroblotted as described in Example 3. The presence of T7-tagged SLIC-1 protein in the samples was detected by Western blot analysis using an anti-T7 Horse Radish Peroxidase LumiBlot Kit (Novagen) according to the manufacturer's instructions.

Figure 3:
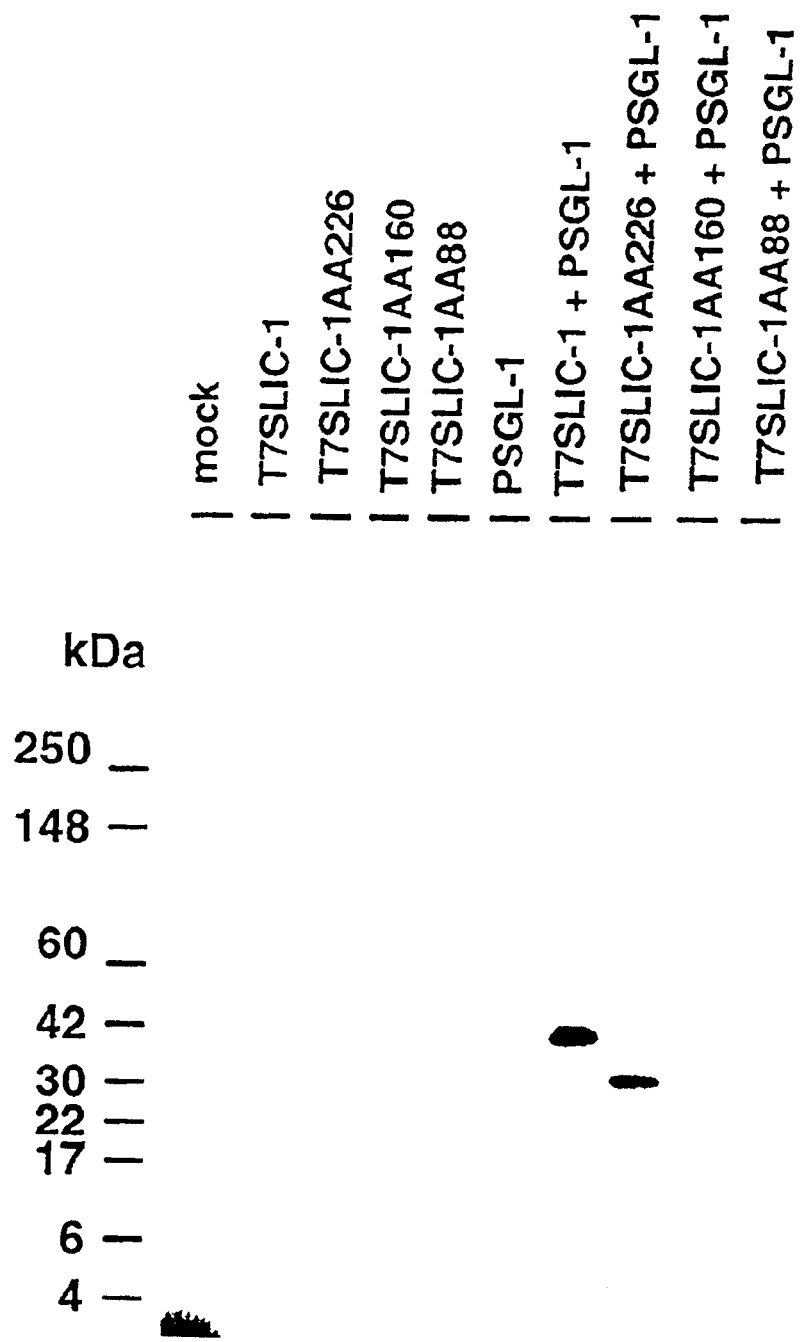
FIG. 3 depicts the co-immunoprecipitation of T7SLIC-1 with PSGL-1 in COS cells.

The results indicate that full length SLIC-1 and a polypeptide comprising amino acid residues 1–226 of SLIC-1 (T7SLIC-1AA226) can be co-immunoprecipitated with PSGL-1 in COS cells, whereas truncated SLIC-1 proteins comprising amino acid residues 1–160 (T7SLIC-1AA160) or 1–88 (T7SLIC-1AA88), respectively, fail to associate with PSGL-1 (FIG. 3). Thus, amino acid residues 1–226 of SLIC-1 are capable of mediating the interaction between SLIC-1 and PSGL-1.

Example 5

Determination of Intron/Exon Boundaries

This example describes the identification of intron exon boundaries in the human and mouse genomic SLIC-1 DNA. FIG. 4 depicts the genomic structures of the human and mouse SLIC-1 genes, which were determined by blast analysis of genomic sequences with human SLIC-1 cDNA sequence.

The human SLIC-1 gene sequence, with the genomic access identifier (X2HTBKPQEQN 23), was identified in a blast search of the Celera™ human genome sequence database using the human cDNA sequence as a query. The human intron sizes and exon positions in cDNA (shown) were determined using full length human cDNA and complete gene sequence. Reference numbers of mouse genomic sequence used are: Exon1 GA__72028902, exon2 GA__66403237, exon3 GA__71266054, and exon4 GA__79541782.

The SLIC-1 gene is composed of four exons in both species. The exon-intron boundaries have been conserved between the human and the mouse. Based on this data, the human chromosomal location of SLIC-1 was determined to be on chromosome 16.

Given the human cDNA sequence of SLIC-1, as described herein, one of skill in the art could determine the murine cDNA and genomic sequence as well as important regulatory sequences of the human and mouse SLIC-1 genes.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for identifying a compound which inhibits the binding of a SLIC-1 protein to PSGL-1, comprising:
   i) contacting said SLIC-1 protein with a test compound; and
   ii) determining the effect of the test compound on the binding of said SLIC-1 protein to PSGL-1;
   wherein said SLIC-1 protein consists of:
   1) a SLIC-1 moiety chosen from:
      (a) amino acids 1–226 of SEQ ID NO:2;
      (b) amino acids 1–316 of SEQ ID NO:2; and
      (c) fragments of (a) or (b) that have PSGL-1 binding activity; and
   2) optionally, at least one heterologous amino acid sequence.

2. A method for identifying a compound which increases the binding of a SLIC-1 protein to PSGL-1, comprising:
   i) contacting said SLIC-1 protein with a test compound; and
   ii) determining the effect of the test compound on the binding of said SLIC-1 protein to PSGL-1;
   wherein said SLIC-1 protein consists of:
   1) a SLIC-1 moiety chosen from:
      (a) amino acids 1–226 of SEQ ID NO:2;
      (b) amino acids 1–316 of SEQ ID NO:2; and
      (c) fragments of (a) or (b) that have PSGL-1 binding activity; and
   2) optionally, at least one heterologous amino acid sequence.

3. The method of claim 1, wherein at least one heterologous sequence is a protein tag.

4. The method of claim 3, wherein said protein tag is a GST tag.

5. The method of claim 3, wherein said protein tag is a T7 tag.

6. The method of claim 1, wherein said SLIC-1 protein consists of amino acids 1–226 of SEQ ID NO:2.

7. The method of claim 1, wherein said SLIC-1 protein consists of amino acids 1–226 of SEQ ID NO:2 and a protein tag.

8. The method of claim 1, wherein said SLIC-1 protein consists of amino acids 1–316 of SEQ ID NO:2.

9. The method of claim 1, wherein said SLIC-1 protein consists of amino acids 1–316 of SEQ ID NO:2 and a protein tag.

10. The method of claim 1, wherein said SLIC-1 protein consists of a fragment of amino acids 1-226 of SEQ ID NO:2, wherein said fragment has PSGL-1 binding activity.

11. The method of claim 1, wherein said SLIC-1 protein consists of a fragment of amino acids 1-226 of SEQ ID NO:2, wherein said fragment has PSGL-1 binding activity, and a protein tag.

12. The method of claim 1, wherein said SLIC-1 protein consists of a fragment of amino acids 1–316 of SEQ ID NO:2, wherein said fragment has PSGL-1 binding activity.

13. The method of claim 1, wherein said SLIC-1 protein consists of a fragment of amino acids 1–316 of SEQ ID NO:2, wherein said fragment has PSGL-1 binding activity, and a protein tag.

14. The method of claim 2, wherein at least one heterologous sequence is a protein tag.

15. The method of claim 14, wherein said protein tag is a GST tag.

16. The method of claim 14, wherein said protein tag is a T7 tag.

17. The method of claim 2, wherein said SLIC-1 protein consists of amino acids 1–226 of SEQ ID NO:2.

18. The method of claim 2, wherein said SLIC-1 protein consists of amino acids 1–226 of SEQ ID NO:2 and a protein tag.

19. The method of claim 2, wherein said SLIC-1 protein consists of amino acids 1–316 of SEQ ID NO:2.

20. The method of claim 2, wherein said SLIC-1 protein consists of amino acids 1–316 of SEQ ID NO:2 and a protein tag.

21. The method of claim 2, wherein said SLIC-1 protein consists of a fragment of amino acids 1-226 of SEQ ID NO:2, wherein said fragment has PSGL-1 binding activity.

22. The method of claim 2, wherein said SLIC-1 protein consists of a fragment of amino acids 1-226 of SEQ ID NO:2, wherein said fragment has PSGL-1 binding activity, and a protein tag.

23. The method of claim 2, wherein said SLIC-1 protein consists of a fragment of amino acids 1–316 of SEQ ID NO:2, wherein said fragment has PSGL-1 binding activity.

24. The method of claim 2, wherein said SLIC-1 protein consists of a fragment of amino acids 1–316 of SEQ ID NO:2, wherein said fragment has PSGL-1 binding activity, and a protein tag.

25. A method for identifying a compound which inhibits the binding of a SLIC-1 protein to PSGL-1, comprising:
i) contacting said SLIC-1 protein with a test compound; and
ii) determining the effect of the test compound on the binding of said SLIC-1 protein to PSGL-1;
wherein said SLIC-1 protein consists of;
1) a SLIC-1 moiety having PSGL-1 binding activity chosen from:
(a) an amino acid sequence at least 95% identical to amino acids 1–226 of SEQ ID NO:2;
(b) an amino acid sequence at least 95% identical to amino acids 1–316 of SEQ ID NO:2; and
(c) fragments of (a) or (b); and
2) optionally, at least one heterologous amino acid sequence.

26. A method for identifying a compound which increases the binding of a SLIC-1 protein to PSGL-1, comprising:
i) contacting said SLIC-1 protein with a test compound; and
ii) determining the effect of the test compound on the binding of said SLIC-1 protein to PSGL-1;
wherein said SLIC-1 protein consists of:
1) a SLIC-1 moiety having PSGL-1 binding activity chosen from:
(a) an amino acid sequence at least 95% identical to amino acids 1–226 of SEQ ID NO:2;
(b) an amino acid sequence at least 95% identical to amino acids 1–316 of SEQ ID NO:2; and
(c) fragments of (a) or (b); and
2) optionally, at least one heterologous amino acid sequence.

27. The method of claim 25, wherein at least one heterologous sequence is a protein tag.

28. The method of claim 27, wherein said protein tag is a GST tag.

29. The method of claim 27, wherein said protein tag is a T7 tag.

30. The method of claim 25, wherein said SLIC-1 protein consists of an amino acid sequence at least 95% identical to amino acids 1–226 of SEQ ID NO:2.

31. The method of claim 25, wherein said SLIC-1 protein consists of an amino acid sequence at least 95% identical to amino acids 1–226 of SEQ ID NO:2 and a protein tag.

32. The method of claim 25, wherein said SLIC-1 protein consists of an amino acid sequence at least 95% identical to amino acids 1–316 of SEQ ID NO:2.

33. The method of claim 25, wherein said SLIC-1 protein consists of an amino acid sequence at least 95% identical to amino acids 1–316 of SEQ ID NO:2 and a protein tag.

34. The method of claim 25, wherein said SLIC-1 protein consists of a fragment of an amino acid sequence at least 95% identical to amino acids 1-226 of SEQ ID NO:2, wherein said fragment has PSGL-1 binding activity.

35. The method of claim 25, wherein said SLIC-1 protein consists of a fragment of an amino acid sequence at least 95% identical to amino acids 1-226 of SEQ ID NO:2, wherein said fragment has PSGL-1 binding activity, and a protein tag.

36. The method of claim 25, wherein said SLIC-1 protein consists of a fragment of an amino acid sequence at least 95% identical to amino acids 1–316 of SEQ ID NO:2, wherein said fragment has PSGL-1 binding activity.

37. The method of claim 25, wherein said SLIC-1 protein consists of a fragment of an amino acid sequence at least 95% identical to amino acids 1–316 of SEQ ID NO:2, wherein said fragment has PSGL-1 binding activity, and a protein tag.

38. The method of claim 26, wherein at least one heterologous sequence is a protein tag.

39. The method of claim 38, wherein said protein tag is a GST tag.

40. The method of claim 38, wherein said protein tag is a T7 tag.

41. The method of claim 26, wherein said SLIC-1 protein consists of an amino acid sequence at least 95% identical to amino acids 1–226 of SEQ ID NO:2.

42. The method of claim 26, wherein said SLIC-1 protein consists of an amino acid sequence at least 95% identical to amino acids 1–226 of SEQ ID NO:2 and a protein tag.

43. The method of claim wherein said SLIC-1 protein consists of an amino acid sequence at least 95% identical to amino acids 1–316 of SEQ ID NO:2.

44. The method of claim 26, wherein said SLIC-1 protein consists of an amino acid sequence at least 95% identical to amino acids 1–316 of SEQ ID NO:2 and a protein tag.

45. The method of claim 26, wherein said SLIC-1 protein consists of a fragment of an amino acid sequence at least 95% identical to amino acids 1-226 of SEQ ID NO:2, wherein said fragment has PSGL-1 binding activity.

46. The method of claim 26, wherein said SLIC-1 protein consists of a fragment of en amino acid sequence at least 95% identical to amino acids 1-226 of SEQ ID NO:2, wherein said fragment has PSGL-1 binding activity, and a protein tag.

47. The method of claim 26, wherein said SLIC-1 protein consists of a fragment of an amino acid sequence at least 95% identical to amino acids 1–316 of SEQ ID NO:2, wherein said fragment has PSGL-1 binding activity.

48. The method of claim 26, wherein said SLIC-1 protein consists of a fragment of an amino acid sequence at least 95% identical to amino acids 1–316 of SEQ ID NO:2, wherein said fragment has PSGL-1 binding activity, and a protein tag.

* * * * *

UNITED STATES PATENT AND TRADEMARK OFFICE
CERTIFICATE OF CORRECTION

PATENT NO. : 6,852,497 B2  Page 1 of 1
DATED : February 8, 2005
INVENTOR(S) : Lorenz et al.

It is certified that error appears in the above-identified patent and that said Letters Patent is hereby corrected as shown below:

<u>Column 67,</u>
Line 63, "of;" should read -- of: --.

<u>Column 69,</u>
Line 4, "claim wherein" should read -- claim 26, wherein --.
Line 15, "en" should read -- an --.

Signed and Sealed this

Seventeenth Day of May, 2005

JON W. DUDAS
*Director of the United States Patent and Trademark Office*